US012630610B2

(12) United States Patent (10) Patent No.: US 12,630,610 B2
Connolly et al. (45) Date of Patent: May 19, 2026

(54) BINDING MOLECULES SPECIFIC FOR HBV ENVELOPE PROTEIN

(71) Applicant: IMMUNOCORE LIMITED, Abingdon (GB)

(72) Inventors: Mary Marguerita Connolly, Abingdon (GB); Sara Crespillo Torreño, Abingdon (GB); Richard Suckling, Abingdon (GB); Marcin Dembek, Abingdon (GB); Jose Donoso, Abingdon (GB); Katrin Wiederhold, Abingdon (GB); Andrew Knox, Abingdon (GB)

(73) Assignee: IMMUNOCORE LIMITED, Abingdon (GB)

(*) Notice: Subject to any disclaimer, the term of this patent is extended or adjusted under 35 U.S.C. 154(b) by 1257 days.

(21) Appl. No.: 17/599,492

(22) PCT Filed: Mar. 27, 2020

(86) PCT No.: PCT/EP2020/058681
§ 371 (c)(1),
(2) Date: Sep. 28, 2021

(87) PCT Pub. No.: WO2020/193745
PCT Pub. Date: Oct. 1, 2020

(65) Prior Publication Data
US 2022/0143207 A1 May 12, 2022

(30) Foreign Application Priority Data
Mar. 28, 2019 (GB) ...................................... 1904328

(51) Int. Cl.
C07K 16/08 (2026.01)
A61K 47/64 (2017.01)
A61K 47/68 (2017.01)
A61P 31/20 (2006.01)
C07K 14/725 (2006.01)
C07K 16/082 (2026.01)

(52) U.S. Cl.
CPC ........ C07K 16/082 (2013.01); A61K 47/6425 (2017.08); A61K 47/6849 (2017.08); A61P 31/20 (2018.01); C07K 14/7051 (2013.01)

(58) Field of Classification Search
CPC .............. C07K 16/082; C07K 14/7051; C07K 2317/34; C07K 2317/70; C07K 2317/73; C07K 2317/92; C07K 2319/33; C07K 2317/31; C07K 16/2809; C07K 16/2833; A61K 47/6425; A61K 47/6849; A61K 2039/505; A61P 31/20
See application file for complete search history.

(56) References Cited

U.S. PATENT DOCUMENTS

| 6,417,324 | B1 | 7/2002 | Sällberg | |
| 8,143,376 | B2 * | 3/2012 | Boulter ................. | A61K 39/39 |
| | | | | 530/350 |
| 8,603,810 | B2 * | 12/2013 | Bertoletti ............... | A61K 45/06 |
| | | | | 435/325 |
| 2006/0233822 | A1 | 10/2006 | Xia et al. | |
| 2012/0308580 | A1 | 12/2012 | Bertoletti et al. | |
| 2015/0246948 | A1 | 9/2015 | Yuan et al. | |
| 2016/0199479 | A1 | 7/2016 | Su et al. | |
| 2016/0200798 | A1 | 7/2016 | Protzer et al. | |
| 2016/0318988 | A1 | 11/2016 | Knox | |
| 2017/0218043 | A1 | 8/2017 | Hayes et al. | |

FOREIGN PATENT DOCUMENTS

| CN | 102786592 A | 11/2012 |
| CN | 109476723 A | 3/2019 |
| WO | WO 1998/039482 A1 | 9/1998 |
| WO | WO 1999/018129 A1 | 4/1999 |
| WO | WO 2001/048145 A2 | 7/2001 |
| WO | WO 2001/062908 A2 | 8/2001 |
| WO | WO 2003/020763 A2 | 3/2003 |
| WO | WO 2004/033685 A1 | 4/2004 |
| WO | WO 2004/044004 A2 | 5/2004 |
| WO | WO 2006/000830 A2 | 1/2006 |
| WO | WO 2010/133828 A1 | 11/2010 |
| WO | WO 2011/062562 A1 | 5/2011 |
| WO | WO 2012/017003 A1 | 2/2012 |
| WO | WO 2014/096803 A1 | 6/2014 |
| WO | WO 2016/174652 A1 | 11/2016 |

(Continued)

OTHER PUBLICATIONS

Chlewicki et. al. High-affinity, Peptide-specific T Cell Receptors can be Generated by Mutations in the CDR1, CDR2, or CDR3, Journal of Mol. Biol. 2005 pp. 223-239 (Year: 2005).*
Rudolph, M. et. al. How TCRs Bind MHCs, Peptides, and Coreceptors, 2006 Ann. Rev. Imm. vol. 24:419-446 (Year: 2006).*
Badri, H., et al., "Optimization of radiation dosing schedules for proneural glioblastoma," Journal of Mathematical Biology, 2016, vol. 72, pp. 1301-1336.

(Continued)

Primary Examiner — Gregory S Emch
Assistant Examiner — Kathleen Cunningchen
(74) Attorney, Agent, or Firm — Fenwick & West LLP

(57) ABSTRACT

The present invention relates to specific binding molecules that bind the HLA-A*02 restricted peptide GLSPTVWLSV (SEQ ID NO: 1) derived from HBV envelope protein. The specific binding molecules may comprise alpha and/or beta TCR variable domains and may comprise non-natural mutations within the alpha and/or beta variable domains relative to a native TCR. The specific binding molecules of the invention are particularly suitable for use as novel immunotherapeutic reagents for the treatment of infectious or malignant disease.

20 Claims, 9 Drawing Sheets

Specification includes a Sequence Listing.

(56) References Cited

FOREIGN PATENT DOCUMENTS

| WO | WO-2016199140 A1 | * 12/2016 | ............... A61P 35/00 |
|----|------|------|------|
| WO | WO 2017/109496 A1 | 6/2017 | |
| WO | WO 2017/158367 A1 | 9/2017 | |
| WO | WO 2018/056897 A1 | 3/2018 | |
| WO | WO 2019/012138 A1 | 1/2019 | |
| WO | WO 2019/051127 A1 | 3/2019 | |

OTHER PUBLICATIONS

Baylot, V., et al., "TCTP Has a Crucial Role in the Different Stages of Prostate Cancer Malignant Progression," Results and Problems in Cell Differentiation, 2017, vol. 64, pp. 255-261.

International Preliminary Report on Patentability, Chapter 1, Patent Cooperation Treaty Application No. PCT/EP2020/058681, Sep. 28, 2021, 10 pages.

International Search Report and Written Opinion, Patent Cooperation Treaty Application No. PCT/EP2020/058681, Jun. 9, 2020, 20 pages.

Muller, S., et al., "Spliceosomal Peptide P140 for Immunotherapy of Systemic Lupus Erythematosus: results of an early phase II clinical trial," *Arthritis and Rheumatism*, vol. 58, Issue 12, Dec. 2008, pp. 3873-3883, https://doi.org/10.1002/art.24027.

Altschul et al., "Basic local alignment search tool," *Journal of Molecular Biology*, vol. 215, Issue 3, Oct. 5, 1990, pp. 403-410.

Altschul et al., "Gapped BLAST and PSI-BLAST: a new generation of protein database search programs," *Nucleic Acids Research*, vol. 25, Issue 17, Sep. 1, 1997, pp. 3389-3402.

Arstila et al., "A Direct Estimate of the Human αβ T Cell Receptor Diversity," *Science*, Oct. 29, 1999, vol. 286, pp. 958-961.

Bossi et al., "Examining the presentation of tumor-associated antigens on peptide-pulsed T2 cells," OncoImmunology, 2013, vol. 2, Issue 11, Article: e26840, 7 pages.

Bragado et al., "Allelic polymorphism in the coding region of human TCR Cα gene and characterization of structural variability in the α chain constant domain," International Immunology, vol. 6, Issue 2, Feb. 1994, pp. 223-230.

Cameron et al., "Identification of a Titin-derived HLA-A1-presented peptide as a cross-reactive target for engineered MAGE A3-directed T cells," *Science Translational Medicine*, Aug. 2013, 5 (197).

Chervin et al., "Engineering higher affinity T cell receptors using a T cell display system," *Journal of Immunological Methods*, vol. 339, Issue 2, Oct. 2008, pp. 175-184.

Davis, M. et al., "Ligand Recognition by 60β T Cell Receptors," Annual Review of Immunology, vol. 16, 1998, pp. 523-544.

Dennis et al., "Albumin Binding as a General Strategy for Improving the Pharmacokinetics of Proteins," *The Journal of Biological Chemistry*, Sep. 20, 2002; vol. 277, No. 38, pp. 35035-35043.

Devereux, et al., "A comprehensive set of sequence analysis programs for the VAX," Nucleic Acids Research, vol. 12, Issue 1, Part 1, Jan. 11, 1984, pp. 387-395.

Dozier et al., "Site-Specific PEGylation of Therapeutic Proteins," *International Journal of Molecular Sciences*, Oct. 28, 2015;16(10):25881-64.

Epel et al., "A functional recombinant single-chain T cell receptor fragment capable of selectively targeting antigen-presenting cells, " Cancer Immunology, Immunotherapy, Nov. 2002, 51(10):565-73.

Folch and Lefranc, "The Human T Cell Receptor Beta Diversity (TRBD) and Beta Joining (TRBJ) Genes," *Experimental and Clinical Immunogenetics*, vol. 17, No. 2, 2000, pp. 107-114.

Folch and Lefranc, "The Human T Cell Receptor Beta Variable (TRBV) Genes," *Experimental and Clinical Immunogenetics*, vol. 17, No. 1, 2000, pp. 42-54.

Hoo et al., "Characterization of a single-chain T-cell receptor expressed in *Escherichia coli*," *Proceedings of the National Academy of Sciences*, May 1992, vol. 89; Issue 10, pp. 4759-4763.

Jefferis, R., "Glycosylation as a strategy to improve antibody-based therapeutics," *Nature Reviews Drug Discovery*, Mar. 2009, vol. 8, pp. 226-234.

Jevsevar et al., "PEGylation of therapeutic proteins," *Biotechnology Journal*, Special Issue: Biotech Methods and Advances, Jan. 2010, vol. 5, Issue 1, pp. 113-128.

Karlin and Altschul, "Applications and statistics for multiple high-scoring segments in molecular sequences," Proceedings of the National Academy of Sciences of the USA, PNAS, Jun. 1993, vol. 90, pp. 5873-5877.

Karlin and Altschul, "Methods for assessing the statistical significance of molecular sequence features by using general scoring schemes," Proceedings of the National Academy of Sciences of the USA, PNAS, Mar. 1990, vol. 87, pp. 2264-2268.

Lefranc, "IMGT®, the International ImmunoGeneTics Information System® for Immunoinformatics," In: Flower, D.R. (eds) Immunoinformatics. Methods in Molecular Biology™, vol. 409, 2007, pp. 19-42.

Lefranc, M. and Lefranc, G., (2001), *T cell Receptor Factsbook*, Academic Press.

Lefranc, M., "IMGT® databases, web resources and tools for immunoglobulin and T cell receptor sequence analysis, http://imgt.cines.fr," (2003), *Leukemia*, 17(1): 260-266.

Lefranc, M., "Nomenclature of the Human T Cell Receptor Genes," *Current Protocols in Immunology*, Supplement 40, Appendix 1, 2001, pp. A.10.1-A.10.23.

O'Connor-Semmes, RL, et al., "GSK2374697, a Novel Albumin-Binding Domain Antibody (AlbudAb), Extends Systemic Exposure of Exendin-4: First Study in Humans—PK/PD and Safety," *Clinical Pharmacology & Therapeutics*, vol. 96, Issue 6, Mitochondrial Pharmacology, Dec. 2014, pp. 704-712.

Park et al., "Hepatitis B Virus—Specific and Global T-Cell Dysfunction in Chronic Hepatitis B," *Gastroenterology*, vol. 150, Issue 3, Dec. 2015, pp. 684-695.

Pearson and Lipman, "Improved tools for biological sequence comparison," Proceedings of the National Academy of Sciences, Apr. 1988, 85 (8) 2444-2448; https://doi.org/10.1073/pnas.85.8.2444.

Robbins, P.F., et al. "Single and Dual Amino Acid Substitutions in TCR CDR's Can Enhance Antigen-Specific T Cell Functions," *The Journal of Immunology*, May 1, 2008, vol. 180, No. 9, pp. 6116-6131.

Robins et al., "Comprehensive assessment of T-cell receptor β-chain diversity in αβ T cells," Blood, Nov. 5, 2009, vol. 114, No. 19, pp. 4099-4107.

Rosenberg et al., "Adoptive cell transfer: a clinical path to effective cancer immunotherapy," *Nature Reviews Cancer*, Apr. 2008, 8(4):299-308.

Scaviner and Lefranc, "The Human T Cell Receptor Alpha Joining (TRAJ) Genes," *Experimental and Clinical Immunogenetics*, vol. 17, No. 2, 2000, pp. 97-106.

Scaviner and Lefranc, "The Human T Cell Receptor Alpha Variable (TRAV) Genes," Experimental and Clinical Immunogenetics, vol. 17, No. 2, 2000, pp. 83-96.

Schellenberger et al., "A recombinant polypeptide extends the in vivo half-life of peptides and proteins in a tunable manner," *Nature Biotechnology*, Dec. 2009, vol. 27, No. 12, pp. 1186-1190.

Schlapschy, M. et al., "PASylation: a biological alternative to PEGylation for extending the plasma half-life of pharmaceutically active proteins," Protein Engineering, Design and Selection, vol. 26, Issue 8, Aug. 2013, pp. 489-501.

Schodin, B. et al., "Binding properties and solubility of single-chain T cell receptors expressed in *E. coli*," *Molecular Immunology*, vol. 33, Issue 9, Jun. 1996, pp. 819-829.

Sinclair, A.M. and Elliott, "Glycoengineering: The effect of glycosylation on the properties of therapeutic proteins," *Journal of Pharmaceutical Sciences*, vol. 94, Issue 8, Aug. 2005, pp. 1626-1635.

Sleep et al., "Albumin as a versatile platform for drug half-life extension," *Biochimica et Biophysica Acta*, vol. 1830, Issue 12, Dec. 2013, pp. 5526-5534.

Stork et al., "A novel tri-functional antibody fusion protein with improved pharmacokinetic properties generated by fusing a bispecific single-chain diabody with an albumin-binding domain from streptococcal protein G," *Protein Engineering, Design and Selection*, vol. 20, Issue 11, Nov. 2007, pp. 569-576, https://doi.org/10.1093/protein/gzm061.

(56) References Cited

OTHER PUBLICATIONS

Torelli and Robotti, "ADVANCE and ADAM: two algorithms for the analysis of global similarity between homologous informational sequences," *Comput. Appl. Biosci.*, vol. 10, Issue 1, Feb. 1994, pp. 3-5, https://doi.org/10.1093/bioinformatics/10.1.3.

Van Roy, M. et al., The preclinical pharmacology of the high affinity anti-IL-6R Nanobody® ALX-0061 supports its clinical development in rheumatoid arthritis, *Arthritis Research & Therapy*, vol. 17, Article No. 135 (2015), 16 pages.

Webster et al., "Longitudinal Analysis of CD8$^+$ T Cells Specific for Structural and Nonstructural Hepatitis B Virus Proteins in Patients with Chronic Hepatitis B: Implications for Immunotherapy," *Journal of Virology*, Jun. 2004, 78(11): 5707-5719.

Weidanz et al., "Display of functional $\alpha\beta$ single-chain T-cell receptor molecules on the surface of bacteriophage," Journal of Immunological Methods, vol. 221, Issues 1-2, Dec. 1998, pp. 59-76.

Willuda, J. et al., "Tumor Targeting of Mono- , Di- , and Tetravalent Anti-p185HER-2 Miniantibodies Multimerized by Self-associating Peptides," *The Journal of Biological Chemistry*, Apr. 2001, vol. 276, Issue 17, pp. 14385-14392.

Ye et al., "T-cell exhaustion in chronic hepatitis B infection: current knowledge and clinical significance," Cell Death & Disease, vol. 6, e1694, Mar. 2015, pp. 1-10; https://doi.org/10.1038/cddis.2015.42.

Zhao, Y. et al., "High-Affinity TCRs Generated by Phage Display Provide CD4+ T Cells with the Ability to Recognize and Kill Tumor Cell Lines," *The Journal of Immunology*, vol. 179, Issue 9, Nov. 1, 2007, pp. 5845-5854.

* cited by examiner

Figure 1

SEQ ID NO: 2 Amino acid sequence of the scaffold alpha chain extracellular region. CDRs are underlined. The extracellular constant region is shown in italics. A non-native cysteine residue is shown in bold (at position 48 of constant region)

```
        10          20          30          40          50          60
AKEVEQNSGP LSVPEGAIAS LNCTYSDRGS QSFFWYRQYS GKSPELIMSI YSNGDKEDGR
        70          80          90          100         110         120
FTAQLNKASQ YVSLLIRDSQ PSDSATYLCA VRNYNTDKLI FGTGTRLQVF PNIQNPDPAV
        130         140         150         160         170         180
YQLRDSKSSD KSVCLFTDFD SQTNVSQSKD SDVYITDKCV LDMRSMDFKS NSAVAWSNKS
        190
DFACANAFNN SIIPEDT
```

SEQ ID NO: 3 Amino acid sequence of the scaffold beta chain extracellular region. CDRs are underlined. The extracellular constant region is shown in italics. A non-native cysteine residue is shown in bold (at position 57 of constant region). Additional non-native amino acids at position 75 and position 89 of the constant region are also shown in bold.

```
        10          20          30          40          50          60
NAGVTQTPKF QVLKTGQSMT LQCAQDMNHE YMSWYRQDPG MGLRLIHYSV GAGITDQGEV
        70          80          90          100         110         120
PNGYNVSRST TEDFPLRLLS AAPSQTSVYF CASSYATGGT GELFFGEGSR LTVLEDLKNV
        130         140         150         160         170         180
FPPEVAVFEP SEAEISHTQK ATLVCLATGF YPDHVELSWW VNGKEVHSGV CTDPQPLKEQ
        190         200         210         220         230         240
PALNDSRYAL SSRLRVSATF WQDPRNHFRC QVQFYGLSEN DEWTQDRAKP VTQIVSAEAW
GRAD
```

Figure 2

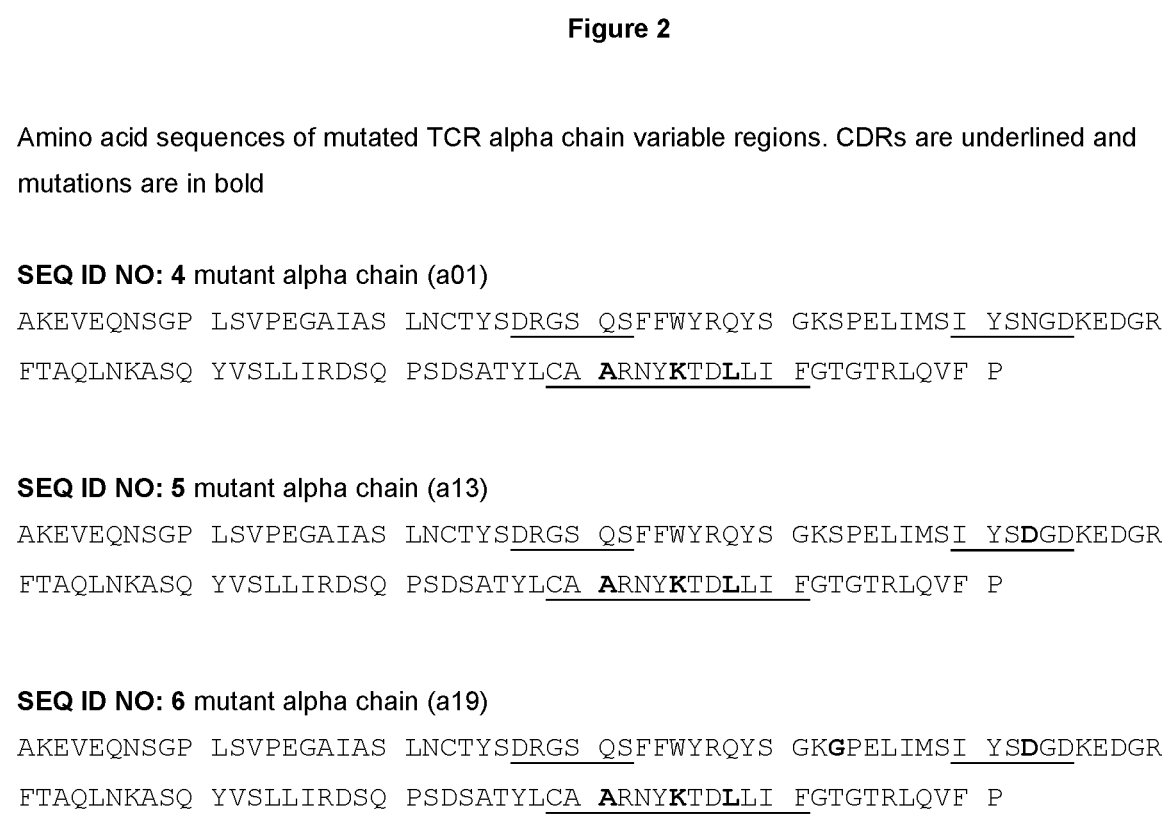

Amino acid sequences of mutated TCR alpha chain variable regions. CDRs are underlined and mutations are in bold

SEQ ID NO: 4 mutant alpha chain (a01)

AKEVEQNSGP LSVPEGAIAS LNCTYS<u>DRGS</u> <u>QS</u>FFWYRQYS GKSPELIMS<u>I</u> <u>YSNGDKEDGR</u>
FTAQLNKASQ YVSLLIRDSQ PSDSATYL<u>CA</u> ARNY<u>K</u>TD<u>LLI</u> FGTGTRLQVF P

SEQ ID NO: 5 mutant alpha chain (a13)

AKEVEQNSGP LSVPEGAIAS LNCTYS<u>DRGS</u> <u>QS</u>FFWYRQYS GKSPELIMS<u>I</u> <u>YSDGDKEDGR</u>
FTAQLNKASQ YVSLLIRDSQ PSDSATYL<u>CA</u> ARNY<u>K</u>TD<u>LLI</u> FGTGTRLQVF P

SEQ ID NO: 6 mutant alpha chain (a19)

AKEVEQNSGP LSVPEGAIAS LNCTYS<u>DRGS</u> <u>QS</u>FFWYRQYS GKGPELIMS<u>I</u> <u>YSDGDKEDGR</u>
FTAQLNKASQ YVSLLIRDSQ PSDSATYL<u>CA</u> ARNY<u>K</u>TD<u>LLI</u> FGTGTRLQVF P

Figure 3

Amino acid sequences of mutated TCR beta chain variable regions. CDRs are underlined. Mutations are in bold

SEQ ID NO: 7 mutant beta chain (b02)

NAGVTQTPKF QVLKTGQSMT LQCAQD<u>LNHG</u> <u>YMSWYRQDPG MGLRLIHYSV</u> GAGITDQGEV
PNGYNVSRST TEDFPLRLLS AAPSQTSVYF <u>CASSYATGGT GVLF</u>FGEGSR LTVL

SEQ ID NO: 8 mutant beta chain (b03)

NAGVTQTPKF QVLKTGQSMT LQCAQDMSH<u>G</u> <u>YMSWYRQDPG MGLRLIHYSV</u> GAGITDQGEV
PNGYNVSRST TEDFPLRLLS AAPSQTSVYF <u>CASSYATGGT GDLF</u>FGEGSR LTVL

SEQ ID NO: 9 mutant beta chain (b04)

NAGVTQTPKF QVLKTGQSMT LQCAQD<u>MNHE</u> <u>YMSWYRQDPG MGLRLIHYSV</u> GAGITDQGEV
PNGYNVSRST TEDFPLRLLS AAPSQTSVYF <u>CASSYATGGT GLLF</u>FGEGSR LTVL

SEQ ID NO: 10 mutant beta chain (b05)

NAGVTQTPKF QVLKTGQSMT LQCAQD<u>MNHE</u> <u>YMSWYRQDPG MGLRLIHYSL</u> GAGITDQGEV
PNGYNVSRST TEDFPLRLLS AAPSQTSVYF <u>CASSYATGGT GDLF</u>FGEGSR LTVL

SEQ ID NO: 11 mutant beta chain (b09)

NAGVTQTPKF QVLKTGQSMT LQCAQDLSH<u>G</u> <u>YMSWYRQDPG MGLRLIHYSV</u> GAGITDQGEV
PNGYNVSRST TEDFPLRLLS AAPSQTSVYF <u>CASSYATGGT GDLF</u>FGEGSR LTVL

Figure 4

Amino acid sequences of TCR-anti-CD3 fusions comprising mutated TCR alpha and beta variable domains

Fusion 1 (a19b03)

SEQ ID NO: 12 alpha chain (a19)

```
AKEVEQNSGP LSVPEGAIAS LNCTYSDRGS QSFFWYRQYS GKGPELIMSI YSDGDKEDGR
FTAQLNKASQ YVSLLIRDSQ PSDSATYLCA ARNYKTDLLI FGTGTRLQVF PNIQNPDPAV
YQLRDSKSSD KSVCLFTDFD SQTNVSQSKD SDVYITDKCV LDMRSMDFKS NSAVAWSNKS
DFACANAFNN SIIPEDT
```

SEQ ID NO: 13 beta chain (b03)

```
AIQMTQSPSS LSASVGDRVT ITCRASQDIR NYLNWYQQKP GKAPKLLIYY TSRLESGVPS
RFSGSGSGTD YTLTISSLQP EDFATYYCQQ GNTLPWTFGQ GTKVEIKGGG GSGGGSGSGG
GSGGGGSGGG SEVQLVESGG GLVQPGGSLR LSCAASGYSF TGYTMNWVRQ APGKGLEWVA
LINPYKGVST YNQKFKDRFT ISVDKSKNTA YLQMNSLRAE DTAVYYCARS GYYGDSDWYF
DVWGQGTLVT VSSGGGGSNA GVTQTPKFQV LKTGQSMTLQ CAQDMSHGYM SWYRQDPGMG
LRLIHYSVGA GITDQGEVPN GYNVSRSTTE DFPLRLLSAA PSQTSVYFCA SSYATGGTGD
LFFGEGSRLT VLEDLKNVFP PEVAVFEPSE AEISHTQKAT LVCLATGFYP DHVELSWWVN
GKEVHSGVCT DPQPLKEQPA LNDSRYALSS RLRVSATFWQ DPRNHFRCQV QFYGLSENDE
WTQDRAKPVT QIVSAEAWGR AD
```

Fusion 2 (a13b03)

SEQ ID NO: 14 alpha chain (a13)

```
AKEVEQNSGP LSVPEGAIAS LNCTYSDRGS QSFFWYRQYS GKSPELIMSI YSDGDKEDGR
FTAQLNKASQ YVSLLIRDSQ PSDSATYLCA ARNYKTDLLI FGTGTRLQVF PNIQNPDPAV
YQLRDSKSSD KSVCLFTDFD SQTNVSQSKD SDVYITDKCV LDMRSMDFKS NSAVAWSNKS
DFACANAFNN SIIPEDT
```

SEQ ID NO: 13 beta chain (b03)

```
AIQMTQSPSS LSASVGDRVT ITCRASQDIR NYLNWYQQKP GKAPKLLIYY TSRLESGVPS
RFSGSGSGTD YTLTISSLQP EDFATYYCQQ GNTLPWTFGQ GTKVEIKGGG GSGGGSGGG
GSGGGGSGGG SEVQLVESGG GLVQPGGSLR LSCAASGYSF TGYTMNWVRQ APGKGLEWVA
LINPYKGVST YNQKFKDRFT ISVDKSKNTA YLQMNSLRAE DTAVYYCARS GYYGDSDWYF
DVWGQGTLVT VSSGGGGSNA GVTQTPKFQV LKTGQSMTLQ CAQDMSHGYM SWYRQDPGMG
LRLIHYSVGA GITDQGEVPN GYNVSRSTTE DFPLRLLSAA PSQTSVYFCA SSYATGGTGD
LFFGEGSRLT VLEDLKNVFP PEVAVFEPSE AEISHTQKAT LVCLATGFYP DHVELSWWVN
GKEVHSGVCT DPQPLKEQPA LNDSRYALSS RLRVSATFWQ DPRNHFRCQV QFYGLSENDE
WTQDRAKPVT QIVSAEAWGR AD
```

Figure 4 cont.

Fusion 3 (a01b03)

SEQ ID NO: 15 alpha chain (a01)

AKEVEQNSGP  LSVPEGAIAS  LNCTYSDRGS  QSFFWYRQYS  GKSPELIMSI  YSNGDKEDGR
FTAQLNKASQ  YVSLLIRDSQ  PSDSATYLCA  ARNYKTDLLI  FGTGTRLQVF  PNIQNPDPAV
YQLRDSKSSD  KSVCLFTDFD  SQTNVSQSKD  SDVYITDKCV  LDMRSMDFKS  NSAVAWSNKS
DFACANAFNN  SIIPEDT

SEQ ID NO: 13 beta chain (b03)

AIQMTQSPSS  LSASVGDRVT  ITCRASQDIR  NYLNWYQQKP  GKAPKLLIYY  TSRLESGVPS
RFSGSGSGTD  YTLTISSLQP  EDFATYYCQQ  GNTLPWTFGQ  GTKVEIKGGG  GSGGGGSGGG
GSGGGGSGGG  SEVQLVESGG  GLVQPGGSLR  LSCAASGYSF  TGYTMNWVRQ  APGKGLEWVA
LINPYKGVST  YNQKFKDRFT  ISVDKSKNTA  YLQMNSLRAE  DTAVYYCARS  GYYGDSDWYF
DVWGQGTLVT  VSSGGGGSNA  GVTQTPKFQV  LKTGQSMTLQ  CAQDMSHGYM  SWYRQDPGMG
LRLIHYSVGA  GITDQGEVPN  GYNVSRSTTE  DFPLRLLSAA  PSQTSVYFCA  SSYATGGTGD
LFFGEGSRLT  VLEDLKNVFP  PEVAVFEPSE  AEISHTQKAT  LVCLATGFYP  DHVELSWWVN
GKEVHSGVCT  DPQPLKEQPA  LNDSRYALSS  RLRVSATFWQ  DPRNHFRCQV  QFYGLSENDE
WTQDRAKPVT  QIVSAEAWGR  AD

Fusion 4 (a13b09)

SEQ ID NO: 14 alpha chain (a13)

AKEVEQNSGP  LSVPEGAIAS  LNCTYSDRGS  QSFFWYRQYS  GKSPELIMSI  YSDGDKEDGR
FTAQLNKASQ  YVSLLIRDSQ  PSDSATYLCA  ARNYKTDLLI  FGTGTRLQVF  PNIQNPDPAV
YQLRDSKSSD  KSVCLFTDFD  SQTNVSQSKD  SDVYITDKCV  LDMRSMDFKS  NSAVAWSNKS
DFACANAFNN  SIIPEDT

SEQ ID NO: 16 beta chain (b09)

AIQMTQSPSS  LSASVGDRVT  ITCRASQDIR  NYLNWYQQKP  GKAPKLLIYY  TSRLESGVPS
RFSGSGSGTD  YTLTISSLQP  EDFATYYCQQ  GNTLPWTFGQ  GTKVEIKGGG  GSGGGGSGGG
GSGGGGSGGG  SEVQLVESGG  GLVQPGGSLR  LSCAASGYSF  TGYTMNWVRQ  APGKGLEWVA
LINPYKGVST  YNQKFKDRFT  ISVDKSKNTA  YLQMNSLRAE  DTAVYYCARS  GYYGDSDWYF
DVWGQGTLVT  VSSGGGGSNA  GVTQTPKFQV  LKTGQSMTLQ  CAQDLSHGYM  SWYRQDPGMG
LRLIHYSVGA  GITDQGEVPN  GYNVSRSTTE  DFPLRLLSAA  PSQTSVYFCA  SSYATGGTGD
LFFGEGSRLT  VLEDLKNVFP  PEVAVFEPSE  AEISHTQKAT  LVCLATGFYP  DHVELSWWVN
GKEVHSGVCT  DPQPLKEQPA  LNDSRYALSS  RLRVSATFWQ  DPRNHFRCQV  QFYGLSENDE
WTQDRAKPVT  QIVSAEAWGR  AD

Figure 8
a)
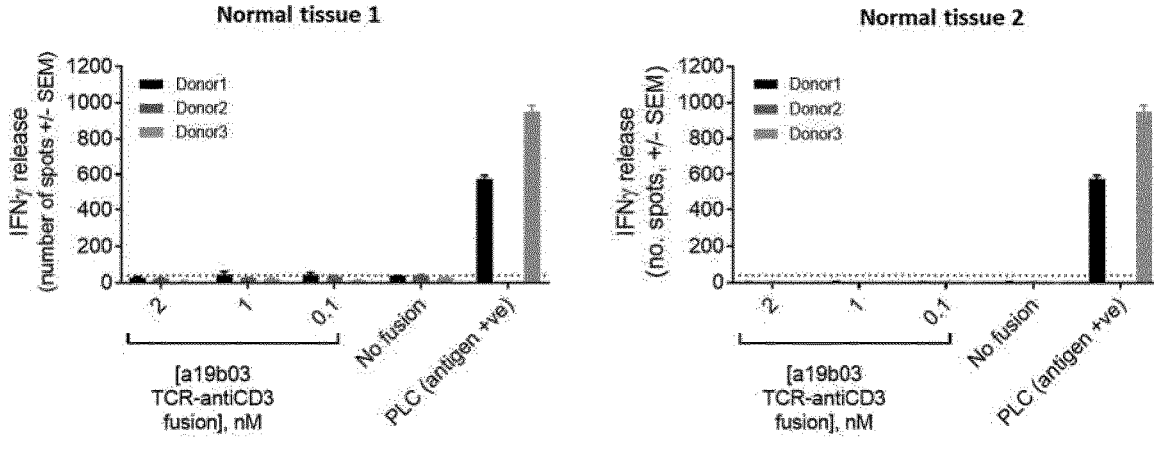
b)
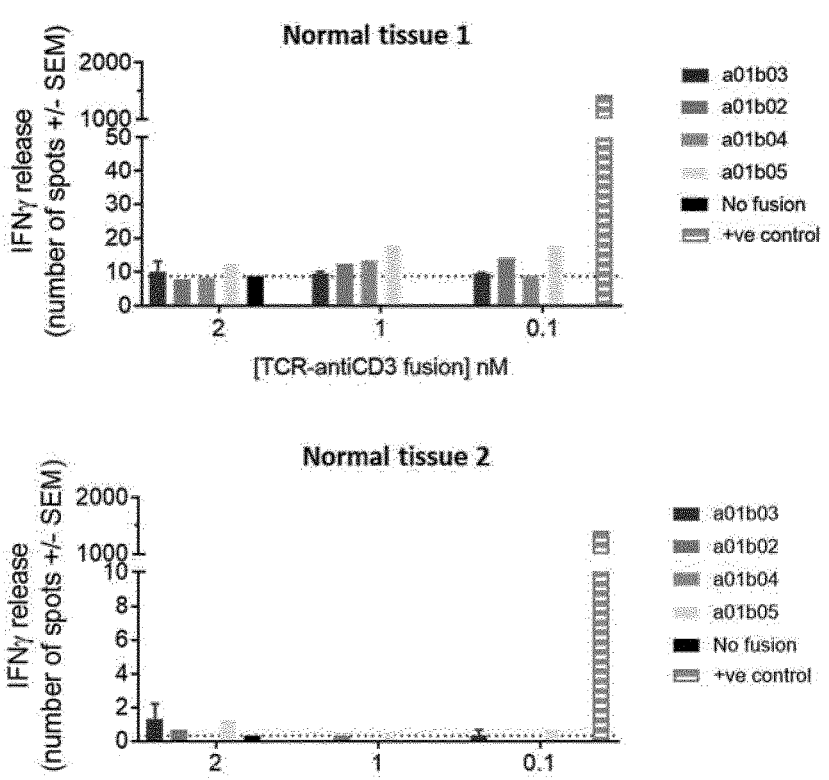

BINDING MOLECULES SPECIFIC FOR HBV ENVELOPE PROTEIN

CROSS-REFERENCE TO RELATED APPLICATIONS

This application is the National Stage of International Application No. PCT/EP2020/058681, filed on Mar. 27, 2020, which claims the benefit of and priority to Great Britain Patent Application Serial No. 1904328.0, filed on Mar. 28, 2019, the contents of which are incorporated by reference in their entirety.

SEQUENCE LISTING

The instant application contains a Sequence Listing which has been submitted via EFS-Web and is hereby incorporated by reference in its entirety. Said ASCII copy, created on Sep. 28, 2021, is named 50018US_CRF_sequencelisting.txt, and is 31,951 bytes in size.

The instant application contains a Sequence Listing which has been submitted electronically in ASCII format and is hereby incorporated by reference in its entirety. Said ASCII copy, created on Jan. 17, 2025, is named 50018US_CRF_Sequencelisting.txt and is 33,988 bytes in size.

The present invention relates to specific binding molecules that bind the HLA-A*02 restricted peptide GLSPTVWLSV (SEQ ID NO: 1) derived from HBV envelope protein. Said specific binding molecules may comprise alpha and/or beta TCR variable domains. Furthermore, said specific binding molecules may comprise non-natural mutations within the alpha and/or beta variable domains relative to a native TCR. The specific binding molecules and/or alpha and/or beta variable domains of the invention are particularly suitable for use as novel immunotherapeutic reagents for the treatment of infectious or malignant disease.

BACKGROUND TO THE INVENTION

An estimated 257 million people are infected with HBV globally, which represents 3.5% of the total population. The prevalence is highest in the World Health Organisation defined Western Pacific Region and African Region where ~6% of adults are infected. An acute HBV infection can resolve or may develop into a chronic infection, but the likelihood that the infection becomes chronic depends upon the age of the person. Of infants <1 year of age, 80-90% develop chronic infections; of children <6 years of age, 30-50% develop chronic infections; of adults, <5% develop chronic infections.

Chronic hepatitis B is a heterogeneous and refractory disease with poor prognosis, resulting in cirrhosis (scarring of the liver) or cancer in 20-30% of infected adults. An effective and safe vaccine to prevent HBV infection has been available since the 1980s. However, many of those living with HBV were born before the introduction of the HBV vaccine and the implementation of early vaccination schedules; the World Health Organisation estimates that of the chronically infected adults 65 million may be women of childbearing age at risk for passing on the infection to their babies. Unlike TB and HIV, mortality from viral is expected to increase due to complications from cirrhosis and hepatocellular carcinoma (HCC) especially in those who are undiagnosed.

Clearance of HBV infection is associated with sustained viral control by effector T cells, while progression to chronic infection is believed to be due to a lack of a sufficiently strong and broad virus specific T cell responses. In chronic infection HBV-specific T cells typically have an exhausted phenotype, characterised by poor cytotoxic activity and impaired cytokine production, preventing clearance of the virus (Ye et al., Cell Death Dis. 2015 March; 6(3): e1694; Park et al., Gastroenterology. 2016 March: 150(3):684-695.e5). Current management of chronic HBV involves treatment with oral antivirals, like tenofovir or entecavir; however, while antivirals suppress viral replication, which can help slow the progression of permanent and fatal liver damage, they do not eliminate the virus and must be used indefinitely to avoid the risk of viral flairs. Furthermore, long-term use of antivirals is associated with viral resistance and toxicity. Therefore, there is a need to provide new therapies for chronic HBV infections that can overcome the limitations of current treatments, restore T cell mediated response against virally infected cells, and offer a functional cure.

T cell receptors (TCRs) are naturally expressed by CD4$^+$ and CD8$^+$ T cells. TCRs are designed to recognize short peptide antigens that are displayed on the surface of antigen presenting cells in complex with Major Histocompatibility Complex (MHC) molecules (in humans, MHC molecules are also known as Human Leukocyte Antigens, or HLA) (Davis et al., Annu Rev Immunol. 1998; 16:523-44). CD8$^+$ T cells, which are also termed cytotoxic T cells, have TCRs that specifically recognize peptides bound to MHC class I molecules. CD8$^+$ T cells are generally responsible for finding and mediating the destruction of diseased cells, including cancerous and virally infected cells.

The peptide GLSPTVWLSV (SEQ ID NO: 1) corresponds to amino acids 348-357 of the full length HBV envelope protein and is presented on the surface of infected cells in complex with HLA-A*02. T cells that recognise this peptide-HLA complex have been reported (Webster et al., J Virol. 2004 June; 78(11): 5707-5719). The GLSPTVWLSV peptide (SEQ ID NO: 1) shows a high level of sequence conservation across all HBV genotypes, with only slight variably at position 10 (the natural variant GLSPTVWLSA (SEQ ID NO: 17) is present in ~78% of sequences in genotype A). Therefore, the GLSPTVWLSV (SEQ ID NO: 1)-HLA-A*02 complex provides an ideal target for TCR-based immunotherapeutic intervention to address chronic disease.

DESCRIPTION OF THE INVENTION

In a first aspect, the present invention provides a specific binding molecule having the property of binding to GLSPTVWLSV (SEQ ID NO: 1) in complex with HLA-A*02 and/or GLSPTVWLSA (SEQ ID No: 17) in complex with HLA-A*02 and comprising a TCR alpha chain variable domain and/or a TCR beta chain variable domain, each of which comprises FR1-CDR1-FR2-CDR2-FR3-CDR3-FR4 where FR is a framework region and CDR is a complementarity determining region, wherein (a) the alpha chain CDRs have the following sequences:

```
                                    (SEQ ID NO: 18)
        CDR1 - DRGSQS (SEQ ID NO: 19)
        CDR2 - IYSNGD (SEQ ID NO: 20)
        CDR3 - CAVRNYNTDKLIF
``` optionally with one or more mutations therein,
and/or (b) the beta chain CDRs have the following sequences:

```
                                    (SEQ ID NO: 21)
        CDR1 - MNHEY (SEQ ID NO: 22)
        CDR2 - SVGAGI (SEQ ID NO: 23)
        CDR3 - CASSYATGGTGELFF
``` optionally with one or more mutations therein.

The invention provides, for the first time, specific binding molecules including CDRs and variable domains, which bind to the GLSPTVWLSV (SEQ ID NO: 1)-HLA complex. The specific binding molecules or binding fragments thereof may include TCR variable domains, which may correspond to those from a native TCR, or more preferably the TCR variable domains may be engineered. Native TCR variable domains may also be referred to as wild-type, natural, parental, unmutated or scaffold domains. The specific binding molecules or binding fragments can be used to produce molecules with ideal therapeutic properties such as supra-physiological affinity for target, long binding half-life, high specificity for target and good stability. The invention also includes bispecific, or bifunctional, or fusion, molecules that incorporate specific binding molecules or binding fragments thereof and a T cell redirecting moiety. Such molecules can mediate a potent and specific response against HBV infected cells by re-directing and activating non-HBV T-cells, which are not exhausted. Furthermore, the use of specific binding molecules with supra-physiological affinity facilitates recognition and clearance of virally infected cells presenting low levels of peptide-HLA. Alternatively, the specific binding molecules or binding fragments may be incorporated into engineered T cells for adoptive therapy.

The TCR domain sequences defined herein are described with reference to IMGT nomenclature which is widely known and accessible to those working in the TCR field. For example, see: LeFranc and LeFranc, (2001). "T cell Receptor Factsbook", Academic Press; Lefranc, (2011), Cold Spring Harb Protoc 2011(6): 595-603; Lefranc, (2001), Curr Protoc Immunol Appendix 1: Appendix 100; and Lefranc, (2003), Leukemia 17(1): 260-266. Briefly, a3 TCRs consist of two disulphide linked chains. Each chain (alpha and beta) is generally regarded as having two domains, namely a variable and a constant domain. A short joining region connects the variable and constant domains and is typically considered part of the alpha variable region. Additionally, the beta chain usually contains a short diversity region next to the joining region, which is also typically considered part of the beta variable region. The variable domain of each chain is located N-terminally and comprises three Complementarity Determining Regions (CDRs) embedded in a framework sequence (FR). The CDRs comprise the recognition site for peptide-MHC binding. There are several genes coding for alpha chain variable (Va) regions and several genes coding for beta chain variable (Vp) regions, which are distinguished by their framework, CDR1 and CDR2 sequences, and by a partly defined CDR3 sequence. The Va and Vp genes are referred to in IMGT nomenclature by the prefix TRAV and TRBV respectively (Folch and Lefranc, (2000), Exp Clin Immunogenet 17(1): 42-54; Scaviner and Lefranc, (2000), Exp Clin Immunogenet 17(2): 83-96; LeFranc and LeFranc, (2001), "T cell Receptor Factsbook", Academic Press). Likewise there are several joining or J genes, termed TRAJ or TRBJ, for the alpha and beta chain respectively, and for the beta chain, a diversity or D gene termed TRBD (Folch and Lefranc, (2000), Exp Clin Immunogenet 17(2): 107-114; Scaviner and Lefranc, (2000), Exp Clin Immunogenet 17(2): 97-106; LeFranc and LeFranc, (2001), "T cell Receptor Factsbook", Academic Press). The huge diversity of T cell receptor chains results from combinatorial rearrangements between the various V, J and D genes, which include allelic variants, and junctional diversity (Arstila, et al., (1999), Science 286(5441): 958-961; Robins et al., (2009), Blood 114(19): 4099-4107.) The constant, or C, regions of TCR alpha and beta chains are referred to as TRAC and TRBC respectively (Lefranc, (2001), Curr Protoc Immunol Appendix 1: Appendix 10).

In the specific binding molecule of the first aspect, the alpha chain variable domain framework regions may comprise the following framework sequences:

FR1—amino acids 1-26 of SEQ ID NO: 2
FR2—amino acids 33-49 of SEQ ID NO: 2
FR3—amino acids 56-88 of SEQ ID NO: 2
FR4—amino acids 102-111 of SEQ ID NO: 2
or respective sequences having at least 90, 91, 92, 93, 94, 95, 96, 97, 98 or 99% identity to said sequences, and/or the beta chain variable domain framework regions may comprise the following sequences:

FR1—amino acids 1-26 of SEQ ID NO: 3
FR2—amino acids 32-48 of SEQ ID NO: 3
FR3—amino acids 55-90 of SEQ ID NO: 3
FR4—amino acids 106-114 of SEQ ID NO: 3
or respective sequences having at least 90, 91, 92, 93, 94, 95, 96, 97, 98 or 99% identity to said sequences.

The GLSPTVWLSA (SEQ ID No: 17) peptide is a naturally-occurring variant of GLSPTVWLSV (SEQ ID NO: 1) which will be the variant presented in a subset of patients. A specific binding molecule with a dual binding profile may be advantageous when the specific binding molecules of the invention are used in treatment, as it provides coverage of those patients who naturally present the variant peptide. Thus, a larger patient population can be addressed. Specific binding molecules that bind to GLSPTVWLSV (SEQ ID NO: 1) HLA-A*02 complex and that bind to GLSPTVWLSA (SEQ ID No: 17) HLA-A*02 complex are therefore provided herein.

As used herein, the term "specific binding molecule" refers to a molecule capable of binding to a target antigen. Such molecules may adopt a number of different formats as discussed herein.

Furthermore, fragments of the specific binding molecules of the invention are also envisioned. A fragment refers to a portion of the specific binding molecule that retains binding to the target antigen.

The term 'mutations' encompasses substitutions, insertions and deletions. Mutations to a native (also referred to as parental, natural, unmutated wild type, or scaffold) specific binding molecule may include those that increase the binding affinity (ko and/or binding half life) of the specific binding molecule to GLSPTVWLSV (SEQ ID NO: 1)-HLA-A*02 complex and/or to GLSPTVWLSA (SEQ ID NO: 17)-HLA-A*02 complex.

The alpha chain framework regions FR1, FR2, and FR3 may comprise amino acid sequences corresponding to a TRAV12-2*02 chain and/or the beta chain framework regions FR1, FR2 and FR3, may comprise amino acid sequences corresponding to those of a TRBV6-5*01 chain.

The FR4 region may comprise the joining region of the alpha and beta variable chains (TRAJ and TRBJ, respectively). The TRAJ region may comprise amino acid sequences corresponding to those of TRAJ34. The TRBJ region may comprise amino acid sequences corresponding to those of TRBJ2-2 In the TCR alpha chain variable region, there may be at least one mutation. There may be one, two, three, four, five or more, mutations in the alpha chain CDRs. One or more of said mutations may be selected from the following mutations, with reference to the numbering of SEQ ID NO: 2:

| Wild type | Mutation |
|---|---|
| N53 | D |
| V91 | A |
| N95 | K |
| K98 | L |

Thus, there may be any or all of the mutations in the table above, optionally in combination with other mutations The alpha chain CDRs may comprise one of the following groups of mutations (with reference to the numbering of SEQ ID NO: 2):

| 1 | V91A | N95K | K98L | |
|---|---|---|---|---|
| 2 | N53D | V91A | N95K | K98L |

The alpha chain CDR1, CDR2 and CDR3 may be selected from:

| CDR1 | CDR2 | CDR3 |
|---|---|---|
| DRGSQS (SEQ ID No: 18) | IYSNGD (SEQ ID No: 19) | CAVRNYNTDKLIF (SEQ ID No: 20) |
| | IYSDGD (SEQ ID No: 24) | CAARNYKTDLLIF (SEQ ID No: 25) |

In a preferred alpha chain, CDR1 is DRGSQS (SEQ ID NO: 18), CDR2 is IYSNGD (SEQ ID NO: 19) and CDR3 is CAARNYKTDLLIF (SEQ ID NO: 25). In another preferred alpha chain, CDR1 is DRGSQS (SEQ ID NO: 18), CDR2 is IYSDGD (SEQ ID NO: 24) and CDR3 is CAARNYKTDLLIF (SEQ ID NO: 25).

In the TCR beta chain variable region, there may be at least one mutation. There may be one, two, three, four, or five, or more, mutations in the beta chain CDRs. One or more of said mutations may be selected from the following mutations with reference to the numbering of SEQ ID NO: 3

| Wild type | Mutation |
|---|---|
| M27 | L |
| N28 | S |
| E30 | G |
| V50 | L |
| E102 | V or D or L |

Thus, there may be any or all of the mutations in the table above, optionally in combination with other mutations.

The beta chain CDRs may comprise one of the following groups of mutations (with reference to the numbering of SEQ ID NO: 3):

| 1 | M27L | E30G | E102V | |
|---|---|---|---|---|
| 2 | N28S | E30G | E102D | |
| 3 | E102L | | | |
| 4 | V50L | E102D | | |
| 5 | M27L | N28S | E30G | E102D |

The beta chain CDR1, CDR2 and CDR3 may be selected from:

| CDR1 | CDR2 | CDR3 |
|---|---|---|
| LNHGY (SEQ ID No: 26) | SVGAGI (SEQ ID No: 22) | CASSYATGGTGVLFF (SEQ ID No: 30) |
| MSHGY (SEQ ID No: 27) | SLGAGI (SEQ ID No: 29) | CASSYATGGTGDLFF (SEQ ID No: 31) |
| MNHEY (SEQ ID No: 21) | | CASSYATGGTGLLFF (SEQ ID No: 32) |
| LSHGY (SEQ ID No: 28) | | CASSYATGGTGELFF (SEQ ID No: 23) |

In a preferred beta chain, CDR1 is MSHGY (SEQ ID NO: 27), CDR2 is SVGAGI (SEQ ID NO: 22) and CDR3 is CASSYATGGTGDLFF (SEQ ID NO: 31). In another preferred beta chain, CDR1 is LNHGY (SEQ ID NO: 26), CDR2 is SVGAGI (SEQ ID NO: 22) and CDR3 is CASSYATGGTGVLFF (SEQ ID NO: 30).

In another preferred beta chain, CDR1 is MNHEY (SEQ ID NO: 21), CDR2 is SVGAGI (SEQ ID NO: 22) and CDR3 is CASSYATGGTGLLFF (SEQ ID NO: 32).

In another preferred beta chain, CDR1 is MNHEY (SEQ ID NO: 21), CDR2 is SLGAGI (SEQ ID NO: 29) and CDR3 is CASSYATGGTGDLFF (SEQ ID NO: 31).

In another preferred beta chain, CDR1 is LSHGY (SEQ ID NO: 28), CDR2 is SVGAGI (SEQ ID NO: 22) and CDR3 is CASSYATGGTGDLFF (SEQ ID NO: 31).

Preferred pairings of TCR alpha and beta CDRs are shown in the table below:

| | | Alpha | | | Beta | | |
|---|---|---|---|---|---|---|---|
| | CDR1 | CDR2 | CDR3 | CDR1 | CDR2 | CDR3 |
| 1 (a01b02) | DRGSQS (SEQ ID NO: 18) | IYSNGD (SEQ ID NO: 19) | CAARNYKTDLLIF (SEQ ID NO: 25) | LNHGY (SEQ ID NO: 26) | SVGAGI (SEQ ID NO: 22) | CASSYATGGTGVLFF (SEQ ID NO: 30) |

-continued

| | Alpha | | | Beta | | |
|---|---|---|---|---|---|---|
| | CDR1 | CDR2 | CDR3 | CDR1 | CDR2 | CDR3 |
| 2 (a01b03) | DRGSQS (SEQ ID NO: 18) | IYSNGD (SEQ ID NO: 19) | CAARNYKTDLLIF (SEQ ID NO: 25) | MSHGY (SEQ ID NO: 27) | SVGAGI (SEQ ID NO: 22) | CASSYATGGTGDLFF (SEQ ID NO: 31) |
| 3 (a01b04) | DRGSQS (SEQ ID NO: 18) | IYSNGD (SEQ ID NO: 19) | CAARNYKTDLLIF (SEQ ID NO: 25) | MNHEY (SEQ ID NO: 21) | SVGAGI (SEQ ID NO: 22) | CASSYATGGTGLLFF (SEQ ID NO: 32) |
| 4 (a01b05) | DRGSQS (SEQ ID NO: 18) | IYSNGD (SEQ ID NO: 19) | CAARNYKTDLLIF (SEQ ID NO: 25) | MNHEY (SEQ ID NO: 21) | SLGAGI (SEQ ID NO: 29) | CASSYATGGTGDLFF (SEQ ID NO: 31) |
| 5 (a01b09) | DRGSQS (SEQ ID NO: 18) | IYSNGD (SEQ ID NO: 19) | CAARNYKTDLLIF (SEQ ID NO: 25) | LSHGY (SEQ ID NO: 28) | SVGAGI (SEQ ID NO: 22) | CASSYATGGTGDLFF (SEQ ID NO: 31) |
| 6 (a13b03) | DRGSQS (SEQ ID NO: 18) | IYSDGD (SEQ ID NO: 24) | CAARNYKTDLLIF (SEQ ID NO: 25) | MSHGY (SEQ ID NO: 27) | SVGAGI (SEQ ID NO: 22) | CASSYATGGTGDLFF (SEQ ID NO: 31) |
| 7 (a13b09) | DRGSQS (SEQ ID NO: 18) | IYSDGD (SEQ ID NO: 24) | CAARNYKTDLLIF (SEQ ID NO: 25) | LSHGY (SEQ ID NO: 28) | SVGAGI (SEQ ID NO: 22) | CASSYATGGTGDLFF (SEQ ID NO: 31) |

A particularly preferred pairing is combination 6. Another particularly preferred pairing is combination 2.

Mutation(s) within the CDRs preferably improve the binding affinity of the specific binding molecule to the GLSPTVWLSV (SEQ ID NO: 1)-HLA-A*02 complex and/or the GLSPTVWLSA (SEQ ID NO: 17)-HLA-A*02 complex, but may additionally or alternatively confer other advantages such as improved stability in an isolated form and improved specificity. Mutations at one or more positions may additionally or alternatively affect the interaction of an adjacent position with the cognate pMHC complex, for example by providing a more favourable angle for interaction. Mutations may include those that are able to reduce the amount of non-specific binding, i.e. reduce binding to alternative antigens relative to GLSPTVWLSV (SEQ ID NO: 1)-HLA-A*02 and/or to GLSPTVWLSA (SEQ ID NO: 17)-HLA-A*02. Mutations may include those that increase efficacy of folding and/or manufacture. Some mutations may contribute to each of these characteristics, others may contribute to affinity but not to specificity, for example, or to specificity but not to affinity etc.

Typically, at least 5, at least 10, at least 15, or more CDR mutations in total are needed to obtain specific binding molecules with pM affinity for target antigen. At least 5, at least 10 or at least 15 CDR mutations in total may be needed to obtain specific binding molecules with pM affinity for target antigen. Specific binding molecules with pM affinity for target antigen are especially suitable as soluble therapeutics. Specific binding molecules for use in adoptive therapy applications may have lower affinity for target antigen and thus fewer CDR mutations, for example, up to 1, up to 2, up to 5, or more CDR mutations in total. Specific binding molecules for use in adoptive therapy applications may have lower affinity for target antigen and thus fewer CDR mutations, for example, 0 mutations or up to 1, up to 2 or up to 5 CDR mutations in total. In some cases the native (also referred to as unmutated) specific binding molecule may have a sufficiently high affinity for target antigen without the need for mutation. It has been noted that the specific binding molecules of the present invention in their native form have advantageously high affinities, especially when compared to binding molecules that bind cancer peptides in complex with HLA. Without wishing to be bound by any particular theory, the present inventors consider this higher affinity may be due to the fact that the GLSPTVWLSV peptide (SEQ ID NO: 1) is derived from a viral, i.e., non-self source.

Mutations may additionally, or alternatively, be made outside of the CDRs, within the framework regions, such mutations may improve binding, and/or specificity, and/or stability, and/or the yield of a purified soluble form of the specific binding molecule. For example, the specific binding molecule of the invention may, additionally or alternatively, comprise an alpha chain variable domain, wherein the alpha chain variable region FR2 has a S to G mutation at position 43 using the numbering of SEQ ID NO: 2. This mutations was found to increase yield. In addition, a Q to A mutation at position 1 of the alpha chain, using the numbering of SEQ ID NO: 2, was found to improve the efficiency of N-terminal methionine cleavage during production in *E. coli*. Inefficient cleavage may be detrimental for a therapeutic, since it may result in a heterogeneous protein product, and or the presence of the initiation methionine may be immunogenic in humans.

Preferably, the a chain variable domain of the specific binding molecule of the invention may comprise respective framework amino acid sequences that have at least 90%, at least 91%, at least 92%, at least 93%, at least 94%, at least 95%, at least 96%, at least 97%, at least 98% or at least 99% identity to the framework amino acid residues 1-26, 33-49, 56-88, 102-111 of SEQ ID NO: 2. The beta chain variable domain of the specific binding molecule of the invention may comprise respective framework amino acid sequences that have at least 90%, at least 91%, at least 92%, at least 93%, at least 94%, at least 95%, at least 96%, at least 97%, at least 98% or at least 99% identity to the framework amino acid residues 1-26, 32-48, 55-90, 106-114 of SEQ ID NO: 3. Alternatively, the stated percentage identity may be over the framework sequences when considered as a whole.

The alpha chain variable domain may comprise any one of the amino acid sequences of SEQ ID NOs: 4-6 (shown in FIG. 2) and the beta chain variable domain may comprise any one of the amino acid sequences of SEQ ID NOs: 7-11 (shown in FIG. 3).

For example, the specific binding molecule may comprise the following alpha and beta chain pairs.

| Alpha chain variable domain | Beta chain variable domain |
| --- | --- |
| SEQ ID No: 4 | SEQ ID No: 7 |
| SEQ ID No: 4 | SEQ ID No: 8 |
| SEQ ID No: 4 | SEQ ID No: 9 |
| SEQ ID No: 4 | SEQ ID No: 10 |
| SEQ ID No: 4 | SEQ ID No: 11 |
| SEQ ID No: 5 | SEQ ID No: 8 |
| SEQ ID No: 5 | SEQ ID No: 11 |
| SEQ ID No: 6 | SEQ ID No: 8 |

A preferred TCR chain pairing is SEQ ID NO: 6 and SEQ ID NO: 8. A preferred TCR chain pairing is SEQ ID NO: 4 and SEQ ID NO: 8.

Within the scope of the invention are phenotypically silent variants of any specific binding molecule of the invention disclosed herein. As used herein the term "phenotypically silent variants" is understood to refer to a specific binding molecule with a TCR variable domain which incorporates one or more further amino acid changes, including substitutions, insertions and deletions, in addition to those set out above, which specific binding molecule has a similar phenotype to the corresponding specific binding molecule without said change(s). For the purposes of this application, specific binding molecule phenotype comprises binding affinity ($K_D$ and/or binding half-life) and specificity. Preferably, the phenotype for a soluble specific binding molecule associated with an immune effector includes potency of immune activation and purification yield, in addition to binding affinity and specificity. A phenotypically silent variant may have a $K_D$ and/or binding half-life for the GLSPTVWLSV (SEQ ID NO: 1)-HLA-A*02 complex and/ or the GLSPTVWLSA (SEQ ID NO: 17)-HLA-A*02 complex within 50%, or more preferably within 30%, 25% or 20%, of the measured $K_D$ and/or binding half-life of the corresponding specific binding molecule without said change(s), when measured under identical conditions (for example at 25° C. and/or on the same SPR chip). Suitable conditions are further provided in Example 3. As is known to those skilled in the art, it may be possible to produce specific binding molecules that incorporate changes in the variable domains thereof compared to those detailed above without altering the affinity of the interaction with the GLSPTVWLSV (SEQ ID NO: 1)-HLA-A*02 complex and/ or the GLSPTVWLSA (SEQ ID NO: 17)-HLA-A*02 complex, and or other functional characteristics. In particular, such silent mutations may be incorporated within parts of the sequence that are known not to be directly involved in antigen binding (e.g. the framework regions and or parts of the CDRs that do not contact the antigen). Such variants are included in the scope of this invention.

Phenotypically silent variants may contain one or more conservative substitutions and/or one or more tolerated substitutions. By tolerated substitutions it is meant those substitutions which do not fall under the definition of conservative as provided below but are nonetheless phenotypically silent. The skilled person is aware that various amino acids have similar properties and thus are 'conservative'. One or more such amino acids of a protein, polypeptide or peptide can often be substituted by one or more other such amino acids without eliminating a desired activity of that protein, polypeptide or peptide.

Thus the amino acids glycine, alanine, valine, leucine and isoleucine can often be substituted for one another (amino acids having aliphatic side chains). Of these possible substitutions it is preferred that glycine and alanine are used to substitute for one another (since they have relatively short side chains) and that valine, leucine and isoleucine are used to substitute for one another (since they have larger aliphatic side chains which are hydrophobic). Other amino acids which can often be substituted for one another include: phenylalanine, tyrosine and tryptophan (amino acids having aromatic side chains); lysine, arginine and histidine (amino acids having basic side chains); aspartate and glutamate (amino acids having acidic side chains); asparagine and glutamine (amino acids having amide side chains); and cysteine and methionine (amino acids having sulphur containing side chains). It should be appreciated that amino acid substitutions within the scope of the present invention can be made using naturally occurring or non-naturally occurring amino acids. For example, it is contemplated herein that the methyl group on an alanine may be replaced with an ethyl group, and/or that minor changes may be made to the peptide backbone. Whether or not natural or synthetic amino acids are used, it is preferred that only L-amino acids are present.

Substitutions of this nature are often referred to as "conservative" or "semi-conservative" amino acid substitutions. The present invention therefore extends to use of a specific binding molecule comprising any of the amino acid sequence described above but with one or more conservative substitutions and or one or more tolerated substitutions in the sequence, such that the amino acid sequence of the specific binding molecule has at least 90% identity, such as at least 90%, at least 91%, at least 92%, at least 93%, at least 94%, at least 95%, at least 96%, at least 97%, at least 98%, at least 99% or 100% identity, to the specific binding molecule comprising amino acids 1-111 of SEQ ID NOs: 2, 4-6, and/or amino acids 1-114 of SEQ ID NOs: 3, 7-11.

"Identity" as known in the art is the relationship between two or more polypeptide sequences or two or more polynucleotide sequences, as determined by comparing the sequences. In the art, identity also means the degree of sequence relatedness between polypeptide or polynucleotide sequences, as the case may be, as determined by the match between strings of such sequences. While there exist a number of methods to measure identity between two polypeptide or two polynucleotide sequences, methods commonly employed to determine identity are codified in computer programs. Preferred computer programs to determine identity between two sequences include, but are not limited to, GCG program package (Devereux, et al., Nucleic Acids Research, 12, 387 (1984), BLASTP, BLASTN, and FASTA (Atschul et al., J. Molec. Biol. 215, 403 (1990)).

One can use a program such as the CLUSTAL program to compare amino acid sequences. This program compares amino acid sequences and finds the optimal alignment by inserting spaces in either sequence as appropriate. It is possible to calculate amino acid identity or similarity (identity plus conservation of amino acid type) for an optimal alignment. A program like BLASTx will align the longest stretch of similar sequences and assign a value to the fit. It is thus possible to obtain a comparison where several regions of similarity are found, each having a different score. Both types of identity analysis are contemplated in the present invention.

The percent identity of two amino acid sequences or of two nucleic acid sequences is determined by aligning the sequences for optimal comparison purposes (e.g., gaps can be introduced in the first sequence for best alignment with the sequence) and comparing the amino acid residues or nucleotides at corresponding positions. The "best alignment" is an alignment of two sequences which results in the highest percent identity. The percent identity is determined by the number of identical amino acid residues or nucleotides in the sequences being compared (i.e., % identity=number of identical positions/total number of positions×100).

The determination of percent identity between two sequences can be accomplished using a mathematical algorithm known to those of skill in the art. An example of a mathematical algorithm for comparing two sequences is the algorithm of Karlin and Altschul (1990) Proc. Natl. Acad. Sci. USA 87:2264-2268, modified as in Karlin and Altschul (1993) Proc. Natl. Acad. Sci. USA 90:5873-5877. The BLASTn and BLASTp programs of Altschul, et al. (1990) J. Mol. Biol. 215:403-410 have incorporated such an algorithm. Determination of percent identity between two nucleotide sequences can be performed with the BLASTn program. Determination of percent identity between two protein sequences can be performed with the BLASTp program. To obtain gapped alignments for comparison purposes, Gapped BLAST can be utilised as described in Altschul et al. (1997) Nucleic Acids Res. 25:3389-3402. Alternatively, PSI-Blast can be used to perform an iterated search which detects distant relationships between molecules (Id.). When utilising BLAST, Gapped BLAST, and PSI-Blast programs, the default parameters of the respective programs (e.g., BLASTp and BLASTp) AA can be used. See www.ncbi.nlm.nih.gov. Default general parameters may include for example, Word Size=3, Expect Threshold=10. Parameters may be selected to automatically adjust for short input sequences. Another example of a mathematical algorithm utilised for the comparison of sequences is the algorithm of Myers and Miller, CABIOS (1989). The ALIGN program (version 2.0) which is part of the CGC sequence alignment software package has incorporated such an algorithm. Other algorithms for sequence analysis known in the art include ADVANCE and ADAM as described in Torellis and Robotti (1994) Comput. Appl. Biosci., 10:3-5; and FASTA described in Pearson and Lipman (1988) Proc. Natl. Acad. Sci. 85:2444-8. Within FASTA, ktup is a control option that sets the sensitivity and speed of the search. For the purposes of evaluating percent identity in the present disclosure, BLASTp with the default parameters is used as the comparison methodology. In addition, when the recited percent identity provides a non-whole number value for amino acids (i.e., a sequence of 25 amino acids having 90% sequence identity provides a value of "22.5", the obtained value is rounded down to the next whole number, thus "22"). Accordingly, in the example provided, a sequence having 22 matches out of 25 amino acids is within 90% sequence identity.

As will be obvious to those skilled in the art, it may be possible to truncate, or extend, the sequences provided at the C-terminus and/or N-terminus thereof, by 1, 2, 3, 4, 5 or more residues, without substantially affecting the functional characteristics of the specific binding molecule. The sequences provided at the C-terminus and/or N-terminus thereof may be truncated or extended by 1, 2, 3, 4 or 5 residues. All such variants are encompassed by the present invention.

Mutations, including conservative and tolerated substitutions, insertions and deletions, may be introduced into the sequences provided using any appropriate method including, but not limited to, those based on polymerase chain reaction (PCR), restriction enzyme-based cloning, or ligation independent cloning (LIC) procedures. These methods are detailed in many of the standard molecular biology texts. For further details regarding polymerase chain reaction (PCR) and restriction enzyme-based cloning, see Sambrook & Russell, (2001) Molecular Cloning—A Laboratory Manual (3$^{rd}$ Ed.) CSHL Press. Further information on ligation independent cloning (LIC) procedures can be found in Rashtchian, (1995) Curr Opin Biotechnol 6(1): 30-6. The TCR sequences provided by the invention may be obtained from solid state synthesis, or any other appropriate method known in the art.

The specific binding molecules of the invention have the property of binding the GLSPTVWLSV (SEQ ID NO: 1)-HLA-A*02 complex and/or the GLSPTVWLSA (SEQ ID NO: 17)-HLA-A*02 complex. Specific binding molecules of the invention demonstrate a high degree of specificity for GLSPTVWLSV (SEQ ID NO: 1)-HLA-A*02 complex and/or for GLSPTVWLSA (SEQ ID NO: 17)-HLA-A*02 complex and are thus particularly suitable for therapeutic use. Specificity in the context of specific binding molecules of the invention relates to their ability to recognise HLA-A*02 target cells that are antigen positive, whilst having minimal ability to recognise HLA-A*02 target cells that are antigen negative. In some cases, the specific binding molecules of the invention may bind the complex of target peptide (GLSPTVWLSV (SEQ ID NO: 1) or the variant GLSPTVWLSA (SEQ ID NO: 17)) with particular HLA-A*02 subtypes, including but not limited to HLA-A*0201, HLA-A*0206 or HLA-A*0207.

Specificity can be measured in vitro, for example, in cellular assays such as those described in Example 6. To test specificity, the specific binding molecules may be in soluble form and associated with an immune effector, and/or may be expressed on the surface of cells, such as T cells. Specificity may be determined by measuring the level of T cell activation in the presence of antigen positive and antigen negative target cells. Minimal recognition of antigen negative target cells is defined as a level of T cell activation of less than 20%, preferably less than 10%, preferably less than 5%, and more preferably less than 1%, of the level produced in the presence of antigen positive target cells, when measured under the same conditions and at a therapeutically relevant TCR concentration. For soluble TCRs associated with an immune effector, a therapeutically relevant concentration may be defined as a TCR concentration of $10^{-9}$ M or below, and/or a concentration of up to 100, preferably up to 1000, fold greater than the corresponding EC50 value. Preferably, for soluble specific binding molecules associated with an immune effector there is at least a 100 fold difference in concentration required for T cell activation against antigen positive cells relative to antigen negative cells. Antigen positive cells may be obtained by peptide-pulsing using a suitable peptide concentration to obtain a level of antigen presentation comparable to cancer cells or infected cells (for example, 10-9 M peptide, as described in Bossi et al., (2013) Oncoimmunol. 1; 2 (11):e26840) or, they may naturally present said peptide. Preferably, both antigen positive and antigen negative cells are human cells. Preferably antigen positive cells are human cancer cells with integrated HBV genome or HBV infected cells. Antigen negative cells preferably include those derived from healthy human tissues.

Specificity may additionally, or alternatively, relate to the ability of a specific binding molecule to bind to GLSPTVWLSV (SEQ ID NO: 1) HLA-A*02 complex and/or to GLSPTVWLSA (SEQ ID NO: 17)-HLA-A*02 complex and not to a panel of alternative peptide-HLA complexes. This may, for example, be determined by the Biacore method of Example 3. Said panel may contain at least 5, and preferably at least 10, alternative peptide-HLA-A*02 complexes. The alternative peptides may share a low level of sequence identity with SEQ ID NO: 1 and may be naturally presented. Alternative peptides are preferably derived from proteins expressed in healthy human tissues. Binding of the specific binding molecule to the GLSPTVWLSV (SEQ ID NO: 1)-HLA-A*02 complex and/or the GLSPTVWLSA (SEQ ID NO: 17)-HLA-A*02 complex may be at least 2 fold greater than to other naturally-presented peptide HLA complexes, more preferably at least 10 fold, or at least 50 fold or at least 100 fold greater, even more preferably at least 400 fold greater. Alternative HLAs do not include other natural variants of the GLSPTVWLSV (SEQ ID NO: 1) peptide such as the sequence, GLSPIV-WLSV (SEQ ID NO: 45) and GLSPTVWLLV (SEQ ID NO: 46)).

An alternative or additional approach to determine specific binding molecule specificity may be to identify the peptide recognition motif of the specific binding molecule using sequential mutagenesis, e.g. alanine scanning, of the target peptide. Residues that form part of the binding motif are those that are not permissible to substitution. Non-permissible substitutions may be defined as those peptide positions in which the binding affinity of the specific binding molecule is reduced by at least 50%, or preferably at least 80% relative to the binding affinity for the non-mutated peptide. Such an approach is further described in Cameron et al., (2013), Sci Transl Med. 2013 Aug. 7; 5 (197): 197ra103 and WO2014096803 in connection with TCRs, though it will be appreciated that such methods can also be applied to the specific binding molecules of the present invention. Specific binding molecule specificity in this case may be determined by identifying alternative motif containing peptides, particularly alternative motif containing peptides in the human proteome, and testing these peptides for binding to the specific binding molecule. Binding of the specific binding molecule to one or more alternative peptides may indicate a lack of specificity. In this case further testing of specific binding molecule specificity via cellular assays may be required. A low tolerance for (alanine) substitutions in the central part of the peptide indicate that the TCR has a high specificity and therefore presents a low risk for cross-reactivity with alternative peptides.

Specific binding molecules of the invention may have an ideal safety profile for use as therapeutic reagents. In this case the specific binding molecules may be in soluble form and may preferably be fused to an immune effector. Suitable immune effectors include but are not limited to, cytokines, such as IL-2 and IFN-γ, superantigens and mutants thereof; chemokines such as IL-8, platelet factor 4, melanoma growth stimulatory protein; antibodies, including fragments, derivatives and variants thereof, that bind to antigens on immune cells such as T cells or NK cell (e.g. anti-CD3, anti-CD28 or anti-CD16); and complement activators. An ideal safety profile means that in addition to demonstrating good specificity, the specific binding molecules of the invention may have passed further preclinical safety tests. Examples of such tests include whole blood assays to confirm minimal cytokine release in the presence of whole blood and thus low risk of causing a potential cytokine release syndrome in vivo, and alloreactivity tests to confirm low potential for recognition of alternative HLA types.

Specific binding molecules of the invention may be amenable to high yield purification, particularly specific binding molecules in soluble format. Yield may be determined based on the amount of correctly folded material obtained at the end of the purification process relative to the original culture volume. High yield typically means greater than 1 mg/L, or greater than 2 mg/L, or more preferably greater than 3 mg/L, or greater than 4 mg/L or greater than 5 mg/L, or higher yield.

Specific binding molecules of the invention preferably have a $K_D$ for the GLSPTVWLSV (SEQ ID NO: 1)-HLA-A*02 complex and/or the GLSPTVWLSA (SEQ ID NO: 17)-HLA-A*02 complex of greater than (i.e. stronger than) the native TCR (also referred to as the non-mutated, or scaffold TCR), for example in the range of 1 pM to 1 μM. In one aspect, specific binding molecules of the invention have a $K_D$ for the complex of from about (i.e. +/−10%) 1 pM to about 400 nM, from about 1 pM to about 1000 pM, from about 1 pM to about 500 pM, from about 1 pM to about 100 pM. Said specific binding molecules may additionally, or alternatively, have a binding half-life (T %) for the complex in the range of from about 1 min to about 60 h, from about 20 min to about 50 h, or from about 2 h to about 35 h, or from about 4 hours to about 20 hours. Preferably, specific binding molecules of the invention have a $K_D$ for the GLSPTVWLSV (SEQ ID NO: 1)-HLA-A*02 complex and/or the GLSPTVWLSA (SEQ ID NO: 17)-HLA-A*02 complex of from about 1 pM to about 100 pM and/or a binding half-life from about 4 h to about 20 h. Such high-affinity is preferable for specific binding molecules in soluble format when associated with therapeutic agents and/or detectable labels.

In another aspect, specific binding molecules of the invention may have a $K_D$ for the complex of from about 50 nM to about 200 μM, or from about 100 nM to about 2 μM and/or a binding half-life for the complex of from about 3 sec to about 12 min. Such specific binding molecules may be preferable for adoptive therapy applications.

Methods to determine binding affinity (inversely proportional to the equilibrium constant $K_D$) and binding half life (expressed as T %) are known to those skilled in the art. In a preferred embodiment, binding affinity and binding half-life are determined using Surface Plasmon Resonance (SPR) or Bio-Layer Interferometry (BLI), for example using a BIAcore instrument or Octet instrument, respectively. A preferred method is provided in Example 3. It will be appreciated that doubling the affinity of a specific binding molecule results in halving the $K_D$. T½ is calculated as In2 divided by the off-rate ($k_{off}$). Therefore, doubling of T½ results in a halving in $k_{off}$. $K_D$ and $k_{off}$ values for TCRs are usually measured for soluble forms of the TCR, i.e. those forms which are truncated to remove cytoplasmic and trans-membrane domain residues. To account for variation between independent measurements, and particularly for interactions with dissociation times in excess of 20 hours, the binding affinity and or binding half-life of a given specific binding molecule may be measured several times, for example 3 or more times, using the same assay protocol, and an average of the results taken. To compare binding data between two samples (i.e. two different specific binding molecules and or two preparations of the same specific binding molecule) it is preferable that measurements are made using the same assay conditions (e.g. temperature), such as those described in Example 3.

Certain preferred specific binding molecules of the invention have a binding affinity for, and/or a binding half-life for, the GLSPTVWLSV (SEQ ID NO: 1)-HLA-A*02 complex and/or the GLSPTVWLSA (SEQ ID NO: 17)-HLA-A*02 complex that is substantially higher than that of the native TCR. Increasing the binding affinity of a native TCR often reduces the specificity of the TCR for its peptide-MHC ligand, and this is demonstrated in Zhao et al., (2007) J. Immunol, 179:9, 5845-5854. However, such TCRs of the invention remain specific for the GLSPTVWLSV (SEQ ID NO: 1)-HLA-A*02 complex and/or the GLSPTVWLSA (SEQ ID NO: 17)-HLA-A*02 complex, despite having substantially higher binding affinity than the native TCR.

Certain preferred specific binding molecules are able to generate a highly potent T cell response in vitro against antigen positive cells, in particular those cells presenting low levels of antigen (i.e. in the order of 5-100). Such specific binding molecules may be in soluble form and linked to an immune effector such as an anti-CD3 antibody. The T cell response that is measured may be the release of T cell activation markers such as Interferon γ or Granzyme B, or target cell killing, or other measure of T cell activation, such as T cell proliferation. Preferably a highly potent response is one with $EC_{50}$ value in the pM range, most preferably, 100 μM or lower.

Specific binding molecules of the invention may comprise TCR variable domains that can be αβ heterodimers. In certain cases, the specific binding molecules of the invention may comprise TCR variable domains that can be γδ heterodimers. In other cases, the specific binding molecules of the invention may comprise TCR variable domains that can be αα or ββ homodimers (or γγ or δδ homodimers). Alpha-beta heterodimeric specific binding molecules of the invention may comprise an alpha chain TRAC constant domain sequence and/or a beta chain TRBC1 or TRBC2 constant domain sequence. The constant domains may be full-length by which it is meant that extracellular, transmembrane and cytoplasmic domains are present, or they may be in soluble format (i.e. having no transmembrane or cytoplasmic domains). One or both of the constant domains may contain mutations, substitutions or deletions relative to the native TRAC and/or TRBC1/2 sequences. The term TRAC and TRBC1/2 also encompasses natural polymorphic variants, for example N to K at position 4 of TRAC (Bragado et al International immunology. 1994 February; 6(2):223-30).

For soluble specific binding molecules of the invention, the alpha and beta chain constant domain sequences may be modified by truncation or substitution to delete the native disulphide bond between Cys4 of exon 2 of TRAC and Cys2 of exon 2 of TRBC1 or TRBC2. The alpha and/or beta chain constant domain sequence(s) may have an introduced disulphide bond between residues of the respective constant domains, as described, for example, in WO 03/020763. In a preferred embodiment the alpha and beta constant domains may be modified by substitution of cysteine residues at position Thr 48 of TRAC and position Ser 57 of TRBC1 or TRBC2, the said cysteines forming a disulphide bond between the alpha and beta constant domains of the TCR. TRBC1 or TRBC2 may additionally include a cysteine to alanine mutation at position 75 of the constant domain and an asparagine to aspartic acid mutation at position 89 of the constant domain. One or both of the extracellular constant domains present in an as heterodimer of the invention may be truncated at the C terminus or C termini, for example by up to 15, or up to 10, or up to 8 or fewer amino acids. One or both of the extracellular constant domains present in an as heterodimer of the invention may be truncated at the C terminus or C termini by, for example, up to 15, or up to 10 or up to 8 amino acids. The C terminus of the alpha chain extracellular constant domain may be truncated by 8 amino acids. Soluble specific binding molecules are preferably associated with therapeutic agents and/or detectable labels.

The constant domains of an αβ heterodimeric TCR may be full length, having both transmembrane and cytoplasmic domains. Such TCRs may contain a disulphide bond corresponding to that found in nature between the respective alpha and beta constant domains. Additionally, or alternatively, a non-native disulphide bond may be present between the extracellular constant domains. Said non-native disulphide bonds are further described in WO03020763 and WO06000830. The non-native disulphide bond may be between position Thr 48 of TRAC and position Ser 57 of TRBC1 or TRBC2. One or both of the constant domains may contain one or more mutations substitutions or deletions relative to the native TRAC and/or TRBC1/2 sequences. TCRs with full-length constant domains are preferable for use in adoptive therapy.

Alternatively, rather than full-length or truncated constant domains there may be no TCR constant domains. Accordingly, the specific binding molecule of the invention may be comprised of the variable domains of the TCR alpha and beta chains, optionally with additional domains as described herein.

Additional domains include but are not limited to immune effector domains (such as antibody domains), Fc domains or albumin binding domains.

Specific binding molecules of the invention may be in single chain format. Single chain formats include, but are not limited to, as TCR polypeptides of the Vα-L-Vβ, Vβ-L-Vα, Vα-Cα-L-Vβ, Vα-L-Vβ-Cβ, or Vα-Cα-L-Vβ-Cβ types, wherein Vα and Vβ are TCR α and β variable regions respectively, Cα and Cβ are TCR α and β constant regions respectively, and L is a linker sequence (Weidanz et al., (1998) J Immunol Methods. December 1; 221 (1-2):59-76; Epel et al., (2002), Cancer Immunol Immunother. November; 51(10):565-73; WO 2004/033685; WO9918129). Linker sequences are usually flexible, in that they are made up primarily of amino acids such as glycine, alanine and serine, which do not have bulky side chains likely to restrict flexibility. Alternatively, linkers with greater rigidity may be desirable. Usable or optimum lengths of linker sequences may be easily determined. Often the linker sequence will be less than about 12, such as less than 10, or from 2-10 amino acids in length. The linker may be 1, 2, 3, 4, 5, 6, 7, 8, 9, 10, 11, 12, 13, 14, 15, 16, 17, 18, 19, 20, 21, 22, 23, 24, 25, 26, 27, 28, 29 or 30 amino acids in length. Examples of suitable linkers that may be used multi-domain binding molecules of the invention include, but are not limited to: GGGGS (SEQ ID No: 33), GGGSG (SEQ ID No: 34), GGSGG (SEQ ID No: 35), GSGGG (SEQ ID No: 36), GSGGGP (SEQ ID No: 37), GGEPS (SEQ ID No: 38), GGEGGGP (SEQ ID No: 39), and GGEGGGSEGGGS (SEQ ID No: 40) (as described in WO2010/133828) and GGGSGGGG (SEQ ID NO: 41). Additional linkers may include sequences having one or more of the following sequence motifs: GGGS (SEQ ID NO: 47), GGGGS (SEQ ID NO: 33), TVLRT (SEQ ID NO: 48), TVSSAS (SEQ ID NO: 49) and TVLSSAS (SEQ ID NO: 50). Where present, one or both of the constant domains may be full length, or they may be truncated and/or contain mutations as described above. Preferably single chain TCRs are soluble. In certain embodiments single chain TCRs of the invention may have an introduced disulphide bond between residues of the respective constant domains, as described in WO 2004/033685. Single chain TCRs are further described in WO2004/033685; WO98/39482; WO01/62908; Weidanz et al. (1998) J Immunol Methods 221(1-2): 59-76; Hoo et al. (1992) Proc Natl Acad Sci USA 89(10): 4759-4763; Schodin (1996) Mol Immunol 33(9): 819-829).

The invention also includes particles displaying specific binding molecules of the invention and the inclusion of said particles within a library of particles. Such particles include but are not limited to phage, yeast cells, ribosomes, or mammalian cells. Method of producing such particles and libraries are known in the art (for example see WO2004/044004; WO01/48145, Chervin et al. (2008) J. Immuno. Methods 339.2: 175-184).

Soluble specific binding molecules of the invention are useful for delivering detectable labels or therapeutic agents to antigen presenting cells and tissues containing antigen presenting cells. They may therefore be associated (covalently or otherwise) with a detectable label (for diagnostic purposes wherein the specific binding molecule is used to detect the presence of cells presenting the cognate antigen); and or a therapeutic agent; and or a pharmacokinetic (PK) modifying moiety.

Examples of PK modifying moieties include, but are not limited to, PEG (Dozier et al., (2015) Int J Mol Sci. October 28; 16(10):25831-64 and Jevsevar et al., (2010) Biotechnol J. January; 5(1):113-28), PASylation (Schlapschy et al., (2013) Protein Eng Des Sel. August; 26(8):489-501), albumin, and albumin binding domains, (Dennis et al., (2002) J Biol Chem. September 20; 277(38):35035-43), and/or unstructured polypeptides (Schellenberger et al., (2009) Nat Biotechnol. December; 27(12):1186-90). Further PK modifying moieties include antibody Fc fragments. PK modifying moieties may serve to extend the in vivo half life.

Where an immunoglobulin Fc domain is used, it may be any antibody Fc region. The Fc region is the tail region of an antibody that interacts with cell surface Fc receptors and some proteins of the complement system. The Fc region typically comprises two polypeptide chains both having two or three heavy chain constant domains (termed CH2, CH3 and CH4), and a hinge region. The two chains being linked by disulphide bonds within the hinge region. Fc domains from immunoglobulin subclasses IgG1, IgG2 and IgG4 bind to and undergo FcRn mediated recycling, affording a long circulatory half-life (3-4 weeks). The interaction of IgG with FcRn has been localized in the Fc region covering parts of the CH2 and CH3 domain. Preferred immunoglobulin Fc for use in the present invention include, but are not limited to Fc domains from IgG1 or IgG4. Preferably the Fc domain is derived from human sequences. The Fc region may also preferably include KiH mutations which facilitate dimerization, as well as mutations to prevent interaction with activating receptors i.e. functionally silent molecules. The immunoglobulin Fc domain may be fused to the C or N terminus of the other domains (i.e., the TCR variable domains and or constant domains and or immune effector), in any suitable order or configuration. The immunoglobulin Fc may be fused to the other domains (i.e., the TCR variable domains and or constant domains and or immune effector) via a linker. Linker sequences are usually flexible, in that they are made up primarily of amino acids such as glycine, alanine and serine, which do not have bulky side chains likely to restrict flexibility. Alternatively, linkers with greater rigidity may be desirable. Usable or optimum lengths of linker sequences may be easily determined. Often the linker sequence will be less than about 12, such as less than 10, or from 2-10 amino acids in length. The linker may be 1, 2, 3, 4, 5, 6, 7, 8, 9, 10, 11, 12, 13, 14, 15, 16, 17, 18, 19, 20, 21, 22, 23, 24, 25, 26, 27, 28, 29 or 30 amino acids in length. Examples of suitable linkers that may be used multi-domain binding molecules of the invention include, but are not limited to: GGGGS (SEQ ID No: 33), GGGSG (SEQ ID No: 34), GGSGG (SEQ ID No: 35), GSGGG (SEQ ID No: 36), GSGGGP (SEQ ID No: 37), GGEPS (SEQ ID No: 38), GGEGGGP (SEQ ID No: 39), and GGEGGGSEGGGS (SEQ ID No: 40) (as described in WO2010/133828) and GGGSGGGG (SEQ ID NO: 41). Additional linkers may include sequences having one or more of the following sequence motifs: GGGS (SEQ ID NO: 47), GGGGS (SEQ ID NO: 33), TVLRT (SEQ ID NO: 48), TVSSAS (SEQ ID NO: 49) and TVLSSAS (SEQ ID NO: 50). Where the immunoglobulin Fc is fused to the TCR, it may be fused to either the alpha or beta chains, with or without a linker. Furthermore, individual chains of the Fc may be fused to individual chains of the TCR.

Preferably the Fc region may be derived from the IgG1 or IgG4 subclass. The two chains may comprise CH2 and CH3 constant domains and all or part of a hinge region. The hinge region may correspond substantially or partially to a hinge region from IgG1, IgG2, IgG3 or IgG4. The hinge may comprise all or part of a core hinge domain and all or part of a lower hinge region. Preferably, the hinge region contains at least one disulphide bond linking the two chains.

The Fc region may comprise mutations relative to a WT sequence. Mutations include substitutions, insertions and deletions. Such mutations may be made for the purpose of introducing desirable therapeutic properties. For example, to facilitate heterodimersation, knobs into holes (KiH) mutations maybe engineered into the CH3 domain. In this case, one chain is engineered to contain a bulky protruding residue (i.e. the knob), such as Y, and the other is chain engineered to contain a complementary pocket (i.e. the hole). Suitable positions for KiH mutations are known in the art. Additionally or alternatively mutations may be introduced that abrogate or reduce binding to Fcγ receptors and or increase binding to FcRn, and/or prevent Fab arm exchange, or remove protease sites.

The PK modifying moiety may also be an albumin-binding domain, which may also act to extend half-life. As is known in the art, albumin has a long circulatory half-life of 19 days, due in part to its size, being above the renal threshold, and by its specific interaction and recycling via FcRn. Attachment to albumin is a well-known strategy to improve the circulatory half-life of a therapeutic molecule in vivo. Albumin may be attached non-covalently, through the use of a specific albumin binding domain, or covalently, by conjugation or direct genetic fusion. Examples of therapeutic molecules that have exploited attachment to albumin for improved half-life are given in Sleep et al., Biochim Biophys Acta. 2013 December; 1830(12):5526-34.

The albumin-binding domain may be any moiety capable of binding to albumin, including any known albumin-binding moiety. Albumin binding domains may be selected from endogenous or exogenous ligands, small organic molecules, fatty acids, peptides and proteins that specifically bind albumin. Examples of preferred albumin binding domains include short peptides, such as described in Dennis et al., J Biol Chem. 2002 Sep. 20; 277(38):35035-43 (for example the peptide QRLMEDICLPRWGCLWEDDF (SEQ ID NO: 51)); proteins engineered to bind albumin such as antibodies, antibody fragments and antibody like scaffolds, for example Albudab® (O'Connor-Semmes et al., Clin Pharmacol Ther. 2014 December; 96(6):704-12), commercially provided by GSK and Nanobody® (Van Roy et al., Arthritis Res Ther. 2015 May 20:17:135), commercially provided by Ablynx; and proteins based on albumin binding domains found in nature such as Streptococcal protein G Protein (Stork et al., Eng Des Sel. 2007 November; 20(11):569-76), for example Albumod® commercially provided by Affibody Preferably, albumin is human serum albumin (HSA). The affinity of the albumin binding domain for human albumin may be in the range of picomolar to micromolar. Given the extremely high concentration of albumin in human serum (35-50 mg/ml, approximately 0.6 mM), it is calculated that substantially all of the albumin binding domains will be bound to albumin in vivo.

The albumin-binding moiety may be linked to the C or N terminus of the other domains (i.e., the TCR variable domains and or constant domains and or immune effector) in any suitable order or configuration. The albumin-binding moiety may be linked to the other domains (i.e., the TCR variable domains and or constant domains and or immune effector) via a linker. Linker sequences are usually flexible, in that they are made up primarily of amino acids such as glycine, alanine and serine, which do not have bulky side chains likely to restrict flexibility. Alternatively, linkers with greater rigidity may be desirable. Usable or optimum lengths of linker sequences may be easily determined. Often the linker sequence will be less than about 12, such as less than 10, or from 2-10 amino acids in length. The linker may be 1, 2, 3, 4, 5, 6, 7, 8, 9, 10, 11, 12, 13, 14, 15, 16, 17, 18, 19, 20, 21, 22, 23, 24, 25, 26, 27, 28, 29 or 30 amino acids in length. Examples of suitable linkers that may be used in multi-domain binding molecules of the invention include, but are not limited to: GGGGS (SEQ ID No: 33), GGGSG (SEQ ID No: 34), GGSGG (SEQ ID No: 35), GSGGG (SEQ ID No: 36), GSGGGP (SEQ ID No: 37), GGEPS (SEQ ID No: 38), GGEGGGP (SEQ ID No: 42), and GGEGGGSEGGGS (SEQ ID No: 43) (as described in WO2010/133828) and GGGSGGGG (SEQ ID NO: 44). Additional linkers may include sequences having one or more of the following sequence motifs: GGGS (SEQ ID NO: 47), GGGGS (SEQ ID NO: 33), TVLRT (SEQ ID NO: 48), TVSSAS (SEQ ID NO: 49) and TVLSSAS (SEQ ID NO: 50). Where the albumin-binding moiety is linked to the TCR, it may be linked to either the alpha or beta chains, with or without a linker.

Detectable labels for diagnostic purposes include for instance, fluorescent labels, radiolabels, enzymes, nucleic acid probes and contrast reagents.

For some purposes, the specific binding molecules of the invention may be aggregated into a complex comprising several specific binding molecules to form a multivalent specific binding molecule complex. There are a number of human proteins that contain a multimerisation domain that may be used in the production of multivalent specific binding molecule complexes. For example the tetramerisation domain of p53 which has been utilised to produce tetramers of scFv antibody fragments which exhibited increased serum persistence and significantly reduced off-rate compared to the monomeric scFv fragment (Willuda et al. (2001) J. Biol. Chem. 276 (17) 14385-14392). Haemoglobin also has a tetramerisation domain that could be used for this kind of application. A multivalent specific binding molecule complex of the invention may have enhanced binding capability for the complex compared to a non-multimeric native (also referred to as parental, natural, unmutated wild type, or scaffold) T cell receptor heterodimer of the invention. Thus, multivalent complexes of specific binding molecules of the invention are also included within the invention. Such multivalent specific binding molecule complexes according to the invention are particularly useful for tracking or targeting cells presenting particular antigens in vitro or in vivo, and are also useful as intermediates for the production of further multivalent specific binding molecule complexes having such uses.

Therapeutic agents which may be associated with the specific binding molecules of the invention include immune-modulators and effectors, radioactive compounds, enzymes (perforin for example) or chemotherapeutic agents (cis-platin for example). To ensure that toxic effects are exercised in the desired location the toxin could be inside a liposome linked to the specific binding molecule so that the compound is released slowly. This will prevent damaging effects during the transport in the body and ensure that the toxin has maximum effect after binding of the specific binding molecule to the relevant antigen presenting cells.

Examples of suitable therapeutic agents include, but are not limited to:

small molecule cytotoxic agents, i.e. compounds with the ability to kill mammalian cells having a molecular weight of less than 700 Daltons. Such compounds could also contain toxic metals capable of having a cytotoxic effect. Furthermore, it is to be understood that these small molecule cytotoxic agents also include pro-drugs, i.e. compounds that decay or are converted under physiological conditions to release cytotoxic agents. Examples of such agents include cis-platin, maytansine derivatives, rachelmycin, calicheamicin, docetaxel, etoposide, gemcitabine, ifosfamide, irinotecan, melphalan, mitoxantrone, sorfimer sodiumphotofrin II, temozolomide, topotecan, trimetreate 22arbour22ate, auristatin E vincristine and doxorubicin;

peptide cytotoxins, i.e. proteins or fragments thereof with the ability to kill mammalian cells. For example, ricin, diphtheria toxin, pseudomonas bacterial exotoxin A, Dnase and Rnase;

radio-nuclides, i.e. unstable isotopes of elements which decay with the concurrent emission of one or more of $\alpha$ or $\beta$ particles, or $\gamma$ rays. For example, iodine 131, rhenium 186, indium 111, yttrium 90, bismuth 210 and 213, actinium 225 and astatine 213; chelating agents may be used to facilitate the association of these radio-nuclides to the high affinity TCRs, or multimers thereof;

Immuno-stimulants, i.e. immune effector molecules which stimulate immune response. For example, cytokines such as IL-2 and IFN-$\gamma$, Superantigens and mutants thereof;

TCR-HLA fusions, e.g. fusion to a peptide-HLA complex, wherein said peptide is derived from a common human pathogen, such as Epstein Barr Virus (EBV);

chemokines such as IL-8, platelet factor 4, melanoma growth stimulatory protein, etc;

antibodies or fragments thereof, including anti-T cell or NK cell determinant antibodies (e.g. anti-CD3, anti-CD28 or anti-CD16);

alternative protein scaffolds with antibody like binding characteristics complement activators;

xenogeneic protein domains, allogeneic protein domains, viral/bacterial protein domains, viral/bacterial peptides.

One preferred embodiment is provided by a soluble specific binding molecule of the invention associated (usually by fusion to the N- or C-terminus of the alpha or beta chain, or both, in any suitable configuration) with an immune effector. A particularly preferred immune effector is an anti-CD3 antibody, or a functional fragment or variant of said anti-CD3 antibody. As used herein, the term "antibody" encompasses such fragments and variants. Examples of anti-CD3 antibodies include but are not limited to OKT3, UCHT-1, BMA-031 and 12F6. Antibody fragments and variants/analogues which are suitable for use in the compositions and methods described herein include minibodies, Fab fragments, F(ab')₂ fragments, dsFv and scFv fragments, Nanobodies® (these constructs, marketed by Ablynx (Belgium), comprise synthetic single immunoglobulin variable heavy domain derived from a camelid (e.g. camel or llama) antibody) and Domain Antibodies (Domantis (Belgium), comprising an affinity matured single immunoglobulin variable heavy domain or immunoglobulin variable light domain) or alternative protein scaffolds that exhibit antibody like binding characteristics such as Affibodies (Affibody (Sweden), comprising engineered protein A scaffold) or Anticalins (Pieris (Germany)), comprising engineered anticalins) to name but a few.

In another preferred format of the specific binding molecule, the TCR variable domains and immune effector domains may be alternated on separate polypeptide chains, leading to dimerization. Such formats are described in WO2019012138. In brief, the first polypeptide chain could include (from N to C terminus) a first antibody variable domain followed by a TCR variable domain, optionally followed by a Fc domain. The second chain could include (from N to C terminus) a TCR variable domain followed by a second antibody variable domain, optionally followed by a Fc domain. Given linkers of an appropriate length, the chains would dimerise into a multi-specific molecule, optionally including a Fc domain. Molecules in which domains are located on different chains in this way may also be referred to as diabodies, which are also contemplated herein. Additional chains and domains may be added to form, for example, triabodies.

Accordingly, there is also provided herein a dual specificity polypeptide molecule selected from the group of molecules comprising a first polypeptide chain and a second polypeptide chain, wherein: the first polypeptide chain comprises a first binding region of a variable domain (VD1) of an antibody specifically binding to a cell surface antigen of a human immune effector cell, and a first binding region of a variable domain (VR1) of a TCR specifically binding to an MHC-associated peptide epitope, and a first linker (LINK1) connecting said domains;

the second polypeptide chain comprises a second binding region of a variable domain (VR2) of a TCR specifically binding to an MHC-associated peptide epitope, and a second binding region of a variable domain (VD2) of an antibody specifically binding to a cell surface antigen of a human immune effector cell, and a second linker (LINK2) connecting said domains;

wherein said first binding region (VD1) and said second binding region (VD2) associate to form a first binding site (VD1)(VD2) that binds a cell surface antigen of a human immune effector cell; said first binding region (VR1) and said second binding region (VR2) associate to form a second binding site (VR1)(VR2) that binds said MHC-associated peptide epitope;

wherein said two polypeptide chains are fused to human IgG hinge domains and/or human IgG Fc domains or dimerizing portions thereof; and wherein the said two polypeptide chains are connected by covalent and/or non-covalent bonds between said hinge domains and/or Fc-domains; and wherein said dual specificity polypeptide molecule is capable of simultaneously binding the cell surface molecule and the MHC-associated peptide epitope, and dual specificity polypeptide molecules, wherein the order of the binding regions in the two polypeptide chains is selected from VD1-VR1 and VR2-VD2 or VD1-VR2 and VR1-VD2, or VD2-VR1 and VR2-VD1 or VD2-VR2 and VR1-VD1 and wherein the domains are either connected by LINK1 or LINK2, wherein the MHC-associated peptide epitope is GLSPTVWLSV (SEQ ID NO: 1) or GLSPTVWLSA (SEQ ID NO: 17) and the MHC is HLA-A*02.

Linkage of the specific binding molecule and the anti-CD3 antibody may be via covalent or non-covalent attachment. Covalent attachment may be direct, or indirect via a linker sequence. Linker sequences are usually flexible, in that they are made up primarily of amino acids such as glycine, alanine and serine, which do not have bulky side chains likely to restrict flexibility. Alternatively, linkers with greater rigidity may be desirable. Usable or optimum lengths of linker sequences may be easily determined. Often the linker sequence will be less than about 12, such as less than 10, or from 2-10 amino acids in length. Examples of suitable linkers that may be used in specific binding molecules of the invention include, but are not limited to: GGGGS (SEQ ID No: 33), GGGSG (SEQ ID No: 34), GGSGG (SEQ ID No: 35), GSGGG (SEQ ID No: 36), GSGGGP (SEQ ID No: 37), GGEPS (SEQ ID No: 38), GGEGGGP (SEQ ID No: 39), and GGEGGGSEGGGS (SEQ ID No: 40) (as described in WO2010/133828) and GGGSGGGG (SEQ ID NO: 41). Additional linkers may include sequences having one or more of the following sequence motifs: GGGS (SEQ ID NO: 47), GGGGS (SEQ ID NO: 33), TVLRT (SEQ ID NO: 48), TVSSAS (SEQ ID NO: 49) and TVLSSAS (SEQ ID NO: 50).

Specific embodiments of anti-CD3-specific binding molecule fusion constructs of the invention include those alpha and beta chain pairings in which the alpha chain is composed of a TCR variable domain comprising the amino acid sequence of SEQ ID NOs: 4-6 and/or the beta chain is composed of a TCR variable domain comprising the amino acid sequence of SEQ ID NOs: 7-11. Said alpha and beta chains may further comprise a constant region comprising a non-native disulphide bond. The constant domain of the alpha chain may be truncated by eight amino acids. The N or C terminus of the alpha and or beta chain may be fused to an anti-CD3 scFv antibody fragment via a linker selected from SEQ ID NOs: 33-41. Certain preferred embodiments of such anti-CD3-specific binding molecule fusion constructs are provided in FIG. 4 below:

| Alpha chain | Beta Chain |
| --- | --- |
| SEQ ID No: 12 | SEQ ID No: 13 |
| SEQ ID No: 14 | SEQ ID No: 13 |
| SEQ ID No: 15 | SEQ ID No: 13 |
| SEQ ID No: 14 | SEQ ID No: 16 |

Also included within the scope of the invention are functional variants of said anti-CD3-TCR fusion constructs. Said functional variants preferably have at least 90% identity, such as at least 90%, at least 91%, at least 92%, at least 93%, at least 94%, at least 95%, at least 96%, at least 97%, at least 98%, at least 99% or 100% identity to the reference sequence, but are nonetheless functionally equivalent.

In a further aspect, the present invention provides nucleic acid encoding a specific binding molecule, or specific binding molecule anti-CD3 fusion of the invention. In some embodiments, the nucleic acid is cDNA. In some embodiments the nucleic acid may be mRNA. In some embodiments, the invention provides nucleic acid comprising a sequence encoding an a chain variable domain of a TCR of the invention. In some embodiments, the invention provides nucleic acid comprising a sequence encoding a p chain variable domain of a specific binding molecule of the invention. The nucleic acid may be non-naturally occurring and/or purified and/or engineered. The nucleic acid sequence may be codon optimised, in accordance with expression system utilised. As is known to those skilled in the art, expression systems may include bacterial cells such as E. coli, or yeast cells, or mammalian cells, or insect cells, or they may be cell free expression systems.

In another aspect, the invention provides a vector which comprises nucleic acid of the invention. Preferably the vector is a TCR expression vector. Suitable TCR expression vectors include, for example, gamma-retroviral vectors or, more preferably, lentiviral vectors. Further details can be found in Zhang 2012 and references therein (Zhang et al. Adv Drug Deliv Rev. 2012 Jun. 1; 64(8): 756-762).

The invention also provides a cell harbouring a vector of the invention, preferably a TCR expression vector. Suitable cells include, mammalian cells, preferably immune cells, even more preferably T cells. The vector may comprise nucleic acid of the invention encoding in a single open reading frame, or two distinct open reading frames, encoding the alpha chain and the beta chain respectively. Another aspect provides a cell harbouring a first expression vector which comprises nucleic acid encoding the alpha chain of a specific binding molecule of the invention, and a second expression vector which comprises nucleic acid encoding the beta chain of a specific binding molecule of the invention. Such cells are particularly useful in adoptive therapy. The cells of the invention may be isolated and/or recombinant and/or non-naturally occurring and/or engineered.

Since the specific binding molecules of the invention have utility in adoptive therapy, the invention includes a non-naturally occurring and/or purified and/or or engineered cell, especially a T-cell, presenting a specific binding molecule of the invention. The invention also provides an expanded population of T cells presenting a specific binding molecule of the invention. There are a number of methods suitable for the transfection of T cells with nucleic acid (such as DNA, cDNA or RNA) encoding the specific binding molecules of the invention (see for example Robbins et al., (2008) J Immunol. 180: 6116-6131). T cells expressing the specific binding molecules of the invention will be suitable for use in adoptive therapy-based treatment of cancer or chronic viral infection. As will be known to those skilled in the art, there are a number of suitable methods by which adoptive therapy can be carried out (see for example Rosenberg et al., (2008) Nat Rev Cancer 8(4): 299-308).

As is well-known in the art, proteins (including TCRs) may be subject to post translational modifications. Glycosylation is one such modification, which comprises the covalent attachment of oligosaccharide moieties to defined amino acids in the polypeptide or TCR chain. For example, asparagine residues, or serine/threonine residues are well-known locations for oligosaccharide attachment. The glycosylation status of a particular protein depends on a number of factors, including protein sequence, protein conformation and the availability of certain enzymes. Furthermore, glycosylation status (i.e. oligosaccharide type, covalent linkage and total number of attachments) can influence protein function. Therefore, when producing recombinant proteins, controlling glycosylation is often desirable. Controlled glycosylation has been used to improve antibody based therapeutics. (Jefferis et al., (2009) Nat Rev Drug Discov March; 8(3):226-34). For soluble TCRs of the invention glycosylation may be controlled, by using particular cell lines for example (including but not limited to mammalian cell lines such as Chinese hamster ovary (CHO) cells or human embryonic kidney (HEK) cells), or by chemical modification. Such modifications may be desirable, since glycosylation can improve pharmacokinetics, reduce immunogenicity and more closely mimic a native human protein (Sinclair and Elliott, (2005) Pharm Sci. August; 94(8):1626-35).

For administration to patients, the specific binding molecules of the invention (preferably associated with a detectable label or therapeutic agent or expressed on a transfected T cell), specific binding molecule-anti CD3 fusion molecules, nucleic acids, expression vectors or cells of the invention may be provided as part of a sterile pharmaceutical composition together with one or more pharmaceutically acceptable carriers or excipients. This pharmaceutical composition may be in any suitable form, (depending upon the desired method of administering it to a patient). It may be provided in unit dosage form, will generally be provided in a sealed container and may be provided as part of a kit. Such a kit would normally (although not necessarily) include instructions for use. It may include a plurality of said unit dosage forms.

The pharmaceutical composition may be adapted for administration by any appropriate route, such as parenteral (including subcutaneous, intramuscular, intrathecal or intravenous), enteral (including oral or rectal), inhalation or intranasal routes. Such compositions may be prepared by any method known in the art of pharmacy, for example by mixing the active ingredient with the carrier(s) or excipient(s) under sterile conditions.

Dosages of the substances of the present invention can vary between wide limits, depending upon the disease or disorder to be treated, the age and condition of the individual to be treated, etc. a suitable dose range for a specific binding molecule-anti-CD3 fusion molecules may be in the range of 25 ng/kg to 50 µg/kg or 1 µg to 1 g. A physician will ultimately determine appropriate dosages to be used.

Specific binding molecules, specific binding molecule-anti-CD3 fusion molecules, pharmaceutical compositions, vectors, nucleic acids and cells of the invention may be provided in substantially pure form, for example, at least 80%, at least 85%, at least 90%, at least 91%, at least 92%, at least 93%, at least 94%, at least 95%, at least 96%, at least 97%, at least 98%, at least 99% or 100% pure.

Also provided by the invention are:

A specific binding molecule, specific binding molecule-anti-CD3 fusion molecule, nucleic acid, pharmaceutical composition or cell of the invention for use in medicine, preferably for use in a method of treating chronic HBV or hepatocellular carcinoma (HCC) resulting from chronic HBV infection;

the use of a specific binding molecule, specific binding molecule-anti-CD3 fusion molecule, nucleic acid, pharmaceutical composition or cell of the invention in the manufacture of a medicament for treating chronic HBV or hepatocellular carcinoma (HCC) resulting from chronic HBV infection;

a method of treating cancer or a tumour in a patient, comprising administering to the patient a specific binding molecule, specific binding molecule-anti-CD3 fusion molecule, nucleic acid, pharmaceutical compo-
sition or cell of the invention;
an injectable formulation for administering to a human
subject comprising a specific binding molecule, spe-
cific binding molecule-anti-CD3 fusion molecule,
nucleic acid, pharmaceutical composition or cell of the
invention.

The specific binding molecule, specific binding molecule-
anti-CD3 fusion molecule, nucleic acid, pharmaceutical
composition or cell of the invention may be administered by
injection, such as intravenous, subcutaneous, or direct intra-
tumoral injection. The human subject may be of the HLA-
A*02 subtype. Where treatment of a tumour is contem-
plated, the tumour may be a solid or a liquid tumour.

The method of treatment may further include administer-
ing separately, in combination, or sequentially, one or more
additional anti-viral and or anti-neoplastic agents.

Preferred features of each aspect of the invention are as
for each of the other aspects mutatis mutandis. The prior art
documents mentioned herein are incorporated by reference
to the fullest extent permitted by law.

DESCRIPTION OF THE DRAWINGS

FIG. 1—provides the amino acid sequence of the extra-
cellular regions of a soluble version of the scaffold TCR
alpha and beta chain.

FIG. 2—provides example amino acid sequences of
mutated TCR alpha chain variable regions.

FIG. 3—provides example amino acid sequences of
mutated TCR beta chain variable regions.

FIG. 4—provides amino acid sequences of TCR-antiCD3
fusions comprising certain mutated TCR variable domains
as set out in FIGS. 2 and 3.

FIG. 8—provide cellular data further demonstrating
specificity of TCR-antiCD3 fusion molecules comprising
the mutated TCR variable domains as set out in FIGS. 2 and
3.

Figure 5:
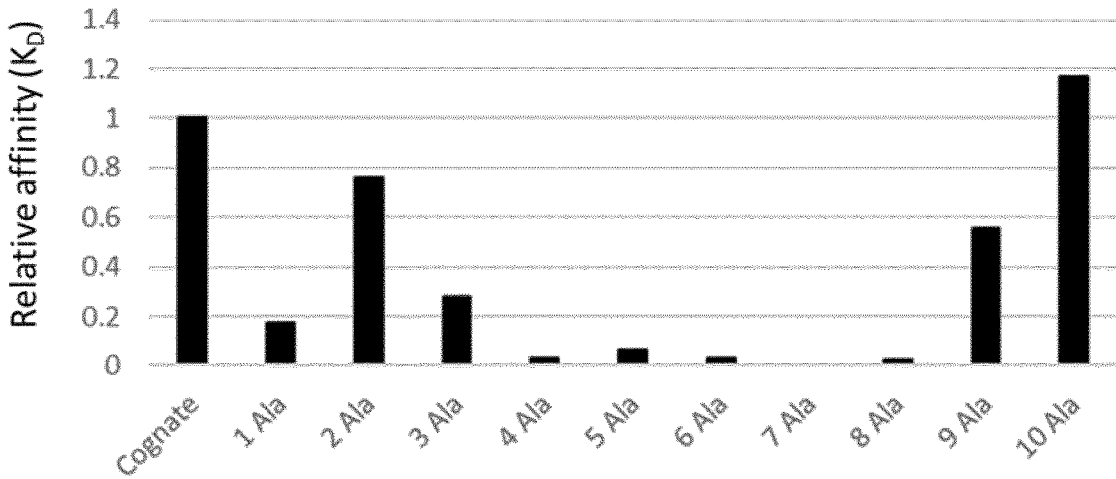
FIG. 5—provides comparative binding data for soluble
WT TCR against alanine substituted peptides.

The invention is further described in the following non-
limiting examples.

Examples

Example 1—Expression, refolding and purification of
WT TCR in soluble format Method DNA sequences encod-
ing the alpha and beta extracellular regions of a soluble TCR
(corresponding to the amino acid sequences in FIG. 1) were
cloned separately into pGMT7-based expression plasmids
using standard methods (as described in Sambrook, et al.
Molecular cloning. Vol. 2. (1989) New York: Cold spring
harbour laboratory press). The expression plasmids were
transformed separately into *E. coli* strain Rosetta (BL21
pLysS). For expression, cells were grown in auto-induction media supplemented with 1% glycerol (+ampicillin 100
µg/ml and 34 µg/ml chloramphenicol) at 230 rpm at 37 C for
2 hours before reducing the temperature to 30 C overnight.
Cells were subsequently harvested by centrifugation. Cell
pellets were lysed with BugBuster protein extraction reagent
(Merck Millipore) according to the manufacturer's instruc-
tions. Inclusion body pellets were recovered by centrifuga-
tion. Pellets were washed twice in Triton buffer (50 mM
Tris-HCl pH 8.1, 0.5% Triton-X100, 100 mM NaCl, 10 mM
NaEDTA) and finally resuspended in detergent free buffer
(50 mM Tris-HCl pH 8.1, 100 mM NaCl, 10 mM NaEDTA).
Inclusion body protein yield was quantified by solubilising
with 6 M guanidine-HCl and measuring $OD_{280}$. Protein
concentration was then calculated using the extinction coef-
ficient. Inclusion body purity was measured by solubilising
with 8 M Urea and loading ~2 µg onto 4-20% SDS-PAGE
under reducing conditions. Purity was then estimated or
calculated using densitometry software (Chemidoc, Biorad).
Inclusion bodies were stored at +4° C. for short term storage
and at −20° C. or −70° C. for longer term storage.

For soluble TCR refolding, a and R chain-containing
inclusion bodies were first mixed and diluted into solubili-
sation/denaturation buffer (6 M Guanidine-hydrochloride,
50 mM Tris HCl pH 8.1, 100 mM NaCl, 10 mM EDTA, 20
mM DTT) followed by incubation for 30 min at 37° C.
Refolding was then initiated by further dilution into refold
buffer (100 mM Tris pH 8.1, 800 or 400 mM L-Arginine
HCL, 2 mM EDTA, 4 M Urea, 6.5 mM cysteamine hydro-
chloride and 1.9 mM cystamine dihydrochloride) and the
solution mixed well. The refolded mixture was dialysed
against 10 L $H_2O$ per L of refold for 18-20 hours at 5° C.±3°
C. After this time, the dialysis buffer was twice replaced with
10 mM Tris pH 8.1 (10 L) and dialysis continued for another
15 hours. The refold mixture was then filtered through 0.45
µm cellulose filters.

Purification of soluble TCRs was initiated by applying the
dialysed refold onto a POROS® 50HQ anion exchange
column and eluting bound protein with a gradient of 0-500
mM NaCl in 20 mM Tris pH 8.1 over 6 column volumes
using an Akta® Pure (GE Healthcare). Peak TCR fractions
were identified by SDS PAGE before being pooled and
concentrated. The concentrated sample was then applied to
a Superdex®200 Increase 10/300 GL gel filtration column
(GE Healthcare) pre-equilibrated in Dulbecco's PBS buffer.
The peak TCR fractions were pooled and concentrated and
the final yield of purified material calculated.

Example 2—Expression, Refolding and Purification
of Soluble TCR-antiCD3 Fusion Molecules Method Preparation of soluble TCR-antiCD3 fusion molecules
was carried out as described in Example 1, except that the
TCR beta chain was fused via a linker to an anti-CD3 single
chain antibody. In addition, the concentration of the redox
reagents in the refolding step were 1 mM cystamine dihy-
drochloride, 10 mM cysteamine hydrochloride). Finally, a
cation exchange step was added following the anion
exchange step. In this case, the peak fractions from anion
exchange were diluted 20-fold in 40 mM MES, and applied
to a POROS® 50HS cation exchange column. Bound pro-
tein was eluted with a gradient of 0-500 mM NaCl in 40 mM
MES. Peak fractions were pooled and adjusted to 200 mM
Tris pH 8.1, before being concentrated and applied directly
to the gel filtration matrix as described in Example 1.

Example 3—Binding Characterisation

Binding analysis of purified soluble TCRs and fusion
molecules to peptide-HLA complex was carried out by surface plasmon resonance, using either a BIAcore 8K, BIAcore 3000 or BIAcore T200 instrument. Biotinylated class I HLA-A*02 molecules were refolded with the peptide of interest and purified using methods known to those in the art (O'Callaghan et al. (1999). Anal Biochem 266(1): 9-15; Garboczi, et al. (1992). Proc Natl Acad Sci USA 89(8): 3429-3433). All measurements were performed at 25° C. in Dulbecco's PBS buffer, supplemented with 0.005% P20.

BIAcore Method

Biotinylated peptide-HLA monomers were immobilized on to streptavidin-coupled CM-5 of Biotin CAPture sensor chips. Equilibrium binding constants were determined using serial dilutions of soluble TCR or fusion molecules injected at a constant flow rate of 10-30 µl min$^{-1}$ over a flow cell coated with ~500 response units (RU) of peptide-HLA-A*02 complex. Equilibrium responses were normalised for each TCR concentration by subtracting the bulk buffer response on a control flow cell containing no peptide-HLA. The $K_D$ value was obtained by non-linear curve fitting using Prism software and the Langmuir binding isotherm, bound=C*Max/(C+KD), where "bound" is the equilibrium binding in RU at injected TCR concentration C and Max is the maximum binding.

For high affinity interactions, binding parameters were determined by single cycle kinetics analysis. Five different concentrations of soluble TCR or fusion protein were injected over a flow cell coated with ~50-200 RU of peptide-HLA complex using a flow rate of 50-60 µl min$^{-1}$. Typically, 60-200 µl of soluble TCR or fusion molecule was injected at a top concentration of between 2-100 nM, with successive 2 fold dilutions used for the other four injections. The lowest concentration was injected first. To measure the dissociation phase, buffer was injected until >10% dissociation occurred, typically after 1-3 hours. Kinetic parameters were calculated using the manufacturer's software. The dissociation phase was fitted to a single exponential decay equation enabling calculation of half-life. The equilibrium constant $K_D$ was calculated from $k_{off}/k_{on}$.

Example 4—Binding Characterisation of the Soluble WT TCR

The soluble WT TCR, having the amino acid sequences shown in FIG. 1, was prepared according to the methods described in Example 1. The yield of purified protein was 9.1 mg/L. Binding parameters were calculated based on equilibrium binding constants according to Example 3. pHLA complexes were prepared comprising either the cognate peptide, a known viral variant of the peptide, or irrelevant peptides.

Results

The soluble WT TCR bound to the cognate peptide GLSPTVWLSV (SEQ ID NO: 1)-HLA-A*02 complex with a $K_D$ of 1.44 µM+/−0.076 µM (Bmax=303; R$^2$=0.997). The same TCR bound to the variant peptide GLSPTVWLSA (SEQ ID NO: 17)-HLA-A*02 with a $K_D$ of 1.23 µM+/−0.07 µM (Bmax=152; R$^2$=0.996). These data indicate that the soluble WT TCR can be used to target both the natural and variant peptide.

Specificity of the soluble WT TCR was assessed against a panel of 24 irrelevant peptide HLA-A*02 complexes that are naturally presented. The irrelevant pHLAs were divided into three groups and loaded onto one of three flow cells. Soluble wild type TCR was injected at concentrations of 68.3 and 6.8 µM over all flow cells. No significant binding was detected at either concentration indicting that the soluble WT TCR is specific for the HLA-A*02 complex.

Additional specificity assessment was carried out using a panel of peptides in which each residue of the GLSPTVWLSV (SEQ ID NO: 1) peptide was sequentially replaced with alanine. Relative binding to each of the alanine substituted peptides was determined and the resulting data are shown in FIG. 5. Alanine substitutions in the central part of the peptide result in loss of TCR binding. A low tolerance for substitutions in the central part of the peptide indicate that the TCR has a high specificity and therefore presents a low risk for cross-reactivity with alternative peptides.

Example 5—Binding Characterisation of Mutated Soluble TCRs Fused to Anti-CD3

The mutated TCR alpha and beta variable domain amino acid sequences provided in FIGS. 2 and 3 respectively (SEQ ID NOs: 4-11) were used to prepare TCR-antiCD3 fusion molecules. Preparation was carried out according to Example 2. FIG. 4 provides full amino acid sequences of four of these TCR-antiCD3 fusion molecules indicated below. The yield of each of these four fusion molecules is shown in brackets a19b03 (6.02 mg/L)
a13b03 (4.13 mg/L)
a01 b03 (3.78) mg/L)
a13b09 (3.46 mg/L)

Binding to peptide-HLA-A*02 complex was determined according to Example 3.

Results

The data presented in the table below show that fusion molecules comprising the indicated TCR variable domain sequences recognised the GLSPTVWLSV (SEQ ID NO: 1)-HLA-A*02 complex with a supra-physiological binding affinity and half-life.

| Alpha chain | Beta chain | $K_D$ (pM) | $t_{1/2}$ (hr) |
|---|---|---|---|
| a01 (SEQ ID NO: 4) | b02 (SEQ ID NO: 7) | 21 | 5.76 |
| a01 (SEQ ID NO: 4) | b03 (SEQ ID NO: 8) | 16 | 11.28 |
| a01 (SEQ ID NO: 4) | b04 (SEQ ID NO: 9) | 19 | 10.78 |
| a01 (SEQ ID NO: 4) | b05 (SEQ ID NO: 10) | 18 | 9.63 |
| a01 (SEQ ID NO: 4) | b09 (SEQ ID NO: 11) | 61.6 | 4.5 |
| a13 (SEQ ID NO: 5) | b03 (SEQ ID NO: 8) | 25.9 | 14.33 |
| a13 (SEQ ID NO: 5) | b09 (SEQ ID NO: 11) | 67.1 | 6.1 |
| a19 (SEQ ID NO: 6) | b03 (SEQ ID NO: 8) | 21 | 14.20 |

Example 6—Potency and Specificity Characterisation of Mutated Soluble TCRs Fused to Anti-CD3

T Cell Activation

Fusion molecules comprising the TCR variable domain sequences as set out in FIGS. 2 and 3 were assessed for their ability to mediate potent and specific activation of CD3+ T cells against cells presenting the GLSPTVWLSV (SEQ ID NO: 1)-HLA-A*02 complex. Interferon-γ (IFN-γ) release was used as a read out for T cell activation.

Method

Assays were performed using a human IFN-γ ELISPOT kit (BD Biosciences) according to the manufacturer's instructions. Briefly, target cells were prepared at a density of 1×10$^6$/ml in assay medium (RPMI 1640 containing 10% heat inactivated FBS and 1% penicillin-streptomycin-L-glutamine) and plated at 50,000 cells per well in a volume of 50 µl. Peripheral blood mononuclear cells (PBMC), isolated from fresh donor blood, were used as effector cells and plated at 50,000 cells per well in a volume of 50 μl (the exact number of cells used for each experiment is donor dependent and may be adjusted to produce a response within a suitable range for the assay). Fusion molecules were titrated to give final concentrations of 10 nM, 1 nM, 0.1 nM, 0.01 nM, 0.001 nM and 0.0001 nM, (spanning the antici-pated clinically relevant range), and added to the well in a volume of 50 μl.

Plates were prepared according to the manufacturer's instructions. Target cells, effector cells and fusion molecules were added to the relevant wells and made up to a final volume of 200 μl with assay medium. All reactions were performed in triplicate. Control wells were also prepared with the omission of fusion molecules. The plates were then incubated overnight (37° C./5% CO$_2$). The next day the plates were washed three times with wash buffer (1×PBS sachet, containing 0.05% Tween-20, made up in deionised water). Primary detection antibody was then added to each well in a volume of 50 μl. Plates were incubated at room temperature for 2 hours prior to being washed again three times. Secondary detection was performed by adding 50 μl of diluted streptavidin-HRP to each well and incubating at room temperature for 1 hour and the washing step repeated. No more than 15 mins prior to use, one drop (20 μl) of AEC chromogen was added to each 1 ml of AEC substrate and mixed and 50 μl added to each well. Spot development was monitored regularly and plates were washed in tap water to terminate the development reaction. The plates were then allowed to dry at room temperature for at least 2 hours prior to counting the spots using a CTL analyser with Immunospot software (Cellular Technology Limited).

In this example, the following cells lines were used as target cells:

PLC/PRF/5 (Antigen Positive)

PLC/PRF/5 is human hepatocellular carcinoma cell line with integrated HBV genome. The GLSPTVWLSV (SEQ ID NO: 1) peptide is naturally presented by these cells (as determined by Mass Spectrometry).

HepG2 (Antigen Negative)

HepG2 is human cell line derived from a liver hepato-cellular carcinoma

Figure 6:
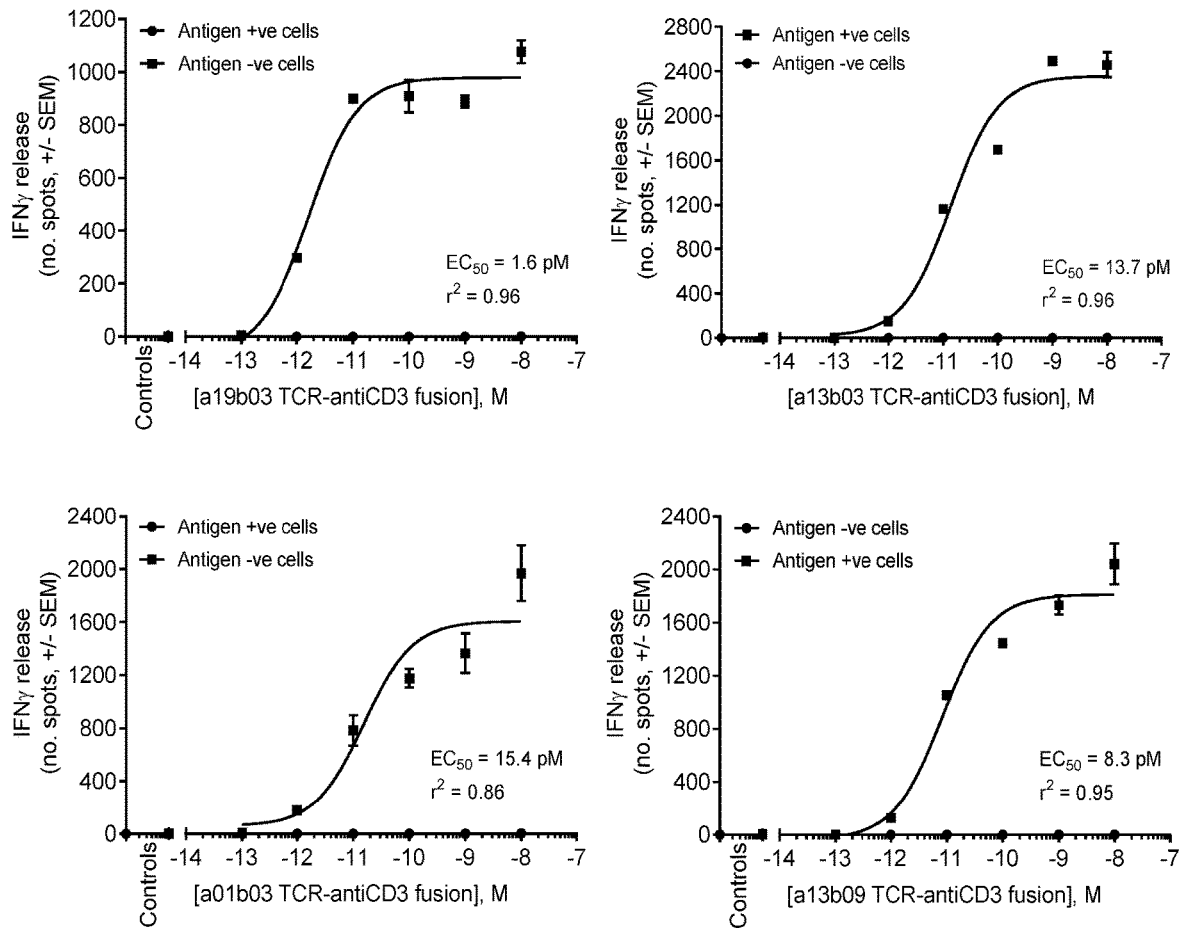
FIG. 6—provides cellular data demonstrating potency and
specificity of TCR-antiCD3 fusion molecules comprising
the mutated TCR variable domains as set out in FIGS. 2 and
3.

Both of the cells lines were transduced with genes encod-ing for HLA-A*02 β$_2$M complex Results Each of the fusion molecules tested demonstrated potent activation of T cells in the presence of antigen positive cells. Ec50 values were calculated from the data and are shown in the table below. The fusion molecules demonstrated no recognition of antigen negative HLA-A*02 positive cells. FIG. 6 shows representative data from four of the fusion molecules listed in the table below (note that value shown were obtained using different effector donors (i.e. not one donor that is common to all).

| Alpha chain | Beta chain | Ec50 (pM) |
| --- | --- | --- |
| a01 (SEQ ID NO: 4) | b02 (SEQ ID NO: 7) | 5.72 |
| a01 (SEQ ID NO: 4) | b03 (SEQ ID NO: 8) | 15.4 |
| a01 (SEQ ID NO: 4) | b04 (SEQ ID NO: 9) | 10.9 |
| a01 (SEQ ID NO: 4) | b05 (SEQ ID NO: 10) | 11 |
| a01 (SEQ ID NO: 4) | b09 (SEQ ID NO: 11) | 14.1 |
| a13 (SEQ ID NO: 5) | b03 (SEQ ID NO: 8) | 13.7 |
| a13 (SEQ ID NO: 5) | b09 (SEQ ID NO: 11) | 8.3 |
| a19 (SEQ ID NO: 6) | b03 (SEQ ID NO: 8) | 1.6 |

These data demonstrate that fusions molecules compris-ing mutated TCR variable domain sequences of the inven-tion can mediate potent (Ec50 in low pM range) and specific T cell activation against antigen positive cells.

Target Cell Killing

The ability of fusion molecules comprising the mutated TCR sequences to mediate potent T cell mediated killing of antigen positive tumour cells was investigated using the IncuCyte platform (Essen BioScience). This assay allows real time detection by microscopy of the release of Caspase-3/7, a marker for apoptosis.

Method

Assays were performed using the CellPlayer 96-well Caspase-3/7 apoptosis assay kit (Essen BioScience, Cat. No. 4440) and carried out according the manufacturer's proto-col. Briefly, PLC/PRF/5 cells were stained with CellTracker DeepRed before plating to allow for 2-colour analysis and subsequently plated at 10,000 cells per well and incubated overnight to allow them to adhere. Fusion molecules were prepared at various concentrations and 25 μl of each was added to the relevant well such that final concentrations were between 100 fM and 10 nM. Effector cells were used at an effector target cell ratio of 10:1 (100,000 cells per well). A control sample without fusion was also prepared along with samples containing either effector cells alone, or target cells alone. NucView assay reagent was made up at 30 μM and 25 μl added to every well and the final volume brought to 150 μl (giving 1.25 μM final conc). The plate was placed in the IncuCyte instrument and images taken every 3 hours (1 image per well) over 5 days. The number of apoptotic cells in each image was determined and recorded as apoptotic cells per mm$^2$. Assays were performed in triplicate.

Results

Figure 7:
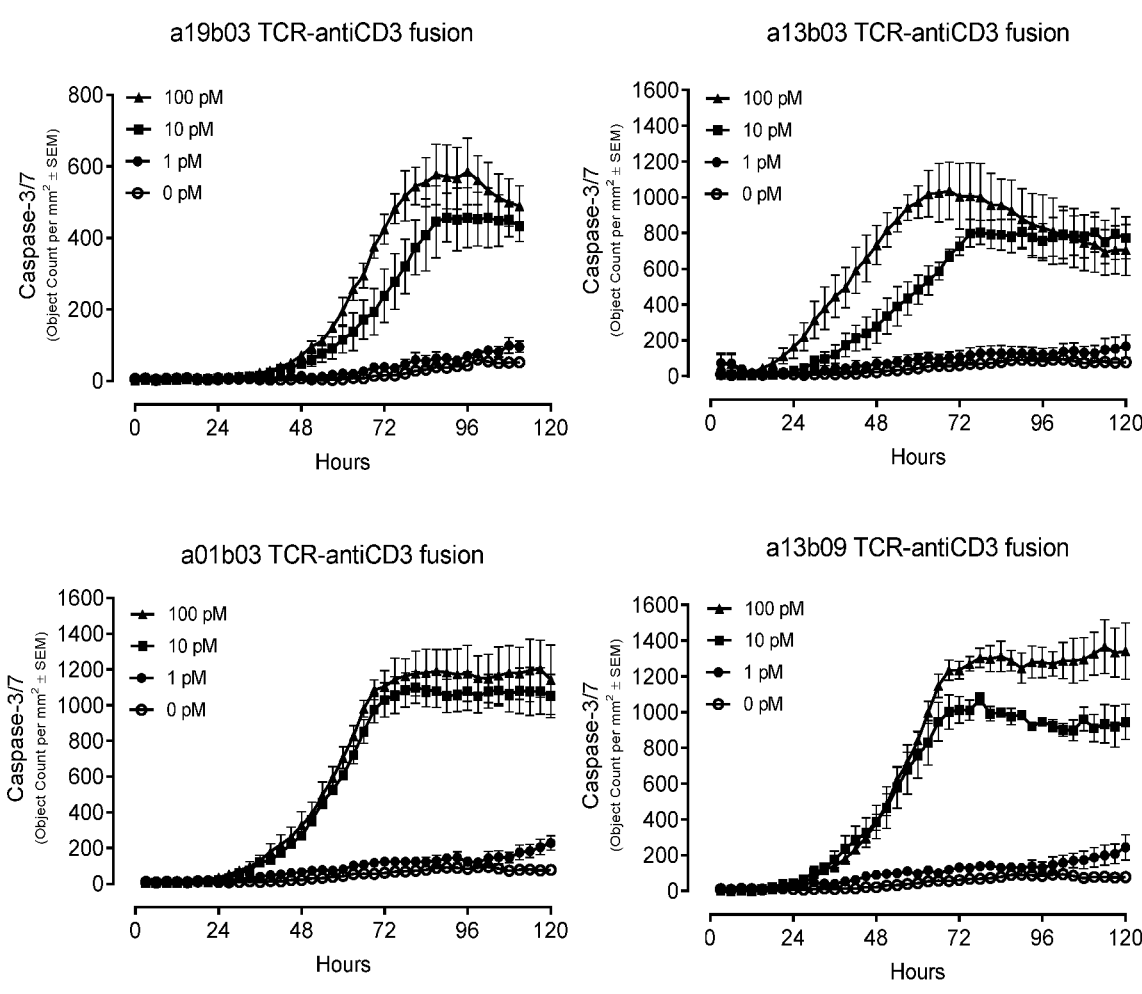
FIG. 7—provides cellular data demonstrating killing of
antigen position cells by TCR-antiCD3 fusion molecules
comprising the mutated TCR variable domains as set out in
FIGS. 2 and 3.

The data presented in FIG. 7 show real-time killing of antigen positive cells in the presence of fusion molecules comprising the mutated TCR variable chain sequences indi-cated on each graph (for clarity only three concentrations are shown). In each case, target cell killing was observed at concentrations of 100 μM or lower. No killing was observed in the absence of fusions molecules.

Safety Screening Against High Risk Normal Tissue

To further demonstrate the specificity of fusion molecules comprising the mutated TCR sequences, further testing was carried out using the same ELISPOT methodology as described above, using a panel of normal cells derived from healthy human tissues as targets.

In a first experiment, a TCR-antiCD3 fusion comprising a19b03 mutated TCR variable domains was tested at three different concentrations (2 nm, 1 nM and 0.1 nM). Two lots of cells from each normal tissue were used as targets, and effector T cells were obtained from 3 different donors. Control measurements were made using a sample without fusion molecule and a sample in which normal cells were replaced with PLC/PRF/5 (antigen positive) cells at a single concentration of fusion molecule (1 nM).

In a second experiment, four different TCR-antiCD3 fusions were used comprising the following mutated chains (a01 b03, a01 b02, a01 b04, a01 b05). The same three concentrations of fusion molecule were used (2 nm, 1 nM and 0.1 nM). A single lot of cells from each normal tissue were used as targets and effector T cells were obtained from a single donor. Control measurements were made using a sample without fusion molecule and a sample in which normal cells were pulsed with 10 μM peptide (antigen positive) and a fusion molecule included at a single con-centration of 0.1 nM.

Results

In both experiments, T cell activation against normal cells was observed at a similar level to background (i.e. taken as sample without fusion molecule).

FIG. 8a shows data from the first experiment for one lot of normal cells from two different tissues and for three different donors (labelled Donor1-3). FIG. 8b shows data from the second experiment for two different tissues. The dotted line in each graph indicates the background level.

These data indicate that fusion molecules comprising the TCR variable domains shown in FIGS. 2 and 3 show no material cross reactivity against a panel of cells derived from normal tissues.

TCR-antiCD3 fusions described have properties that make them particularly suitable for therapeutic use.

Example 7—Potent T Cell Activation Against HBV Infected Cells by Soluble TCRs Fused to Anti-CD3

To demonstrate that that the TCR-antiCD3 fusions of the invention can redirect T cell activity towards HBV infected cells, a HBV infection model was established.

Briefly, the HLA-A*02:01 positive hepatocellular carcinoma (HCC) cell line, HepG2, was transfected with the receptor NTCP. Cells were subsequently infected with 200 MOI of HBV, genotype D ($1\times10^8$ genome copies of lot 03072018, ImQuest BioSciences). Infected cells were then co-cultured with pan T cells obtained from donor blood, in the presence or absence of TCR-antiCD3 fusion. The percentage of infected cells remaining was quantified using PrimeFlow (Invitrogen) to detect Hepatitis B surface antigen (HBsAg) RNA.

TCR-antiCD3 fusions comprising a19b03 and a01b03 were used in this example. In addition, a TCR-antiCD3 specific for an alternative, non-HBV peptide, was used as a negative control Method On day 7 of infection supernatant was removed from wells containing infected HepG2-NTCP cells before pan T cells, with or without TCR-antiCD3 fusion, were added for co-culture. Effector T cells were added at a ratio of 10:1 according to the initial number of HepG2-NTCP plated for infection, and TCR-antiCD3 fusion added at a final concentration of either 1 nM or 0.1 nM. Cells were cultured for 5 days. At the end of co-culture, infected cells were removed from culture plates by trypsin, and surface stained for CD45 and a fixable viability dye (eFluor 780). Following this, cells were fixed and permeabilised for staining of Hepatitis B surface antigen (HBsAg) RNA using the PrimeFlow probeset VF1-6000704. Staining of the housekeeping gene RPL13A was used a positive control for the staining procedure (Probeset VA4-13187). Stained cells were run on the MACSQuant X flow cytometer and analysed by FlowJov10 to quantify the percentage of HBsAg expressing cells.

Results

Figure 9:
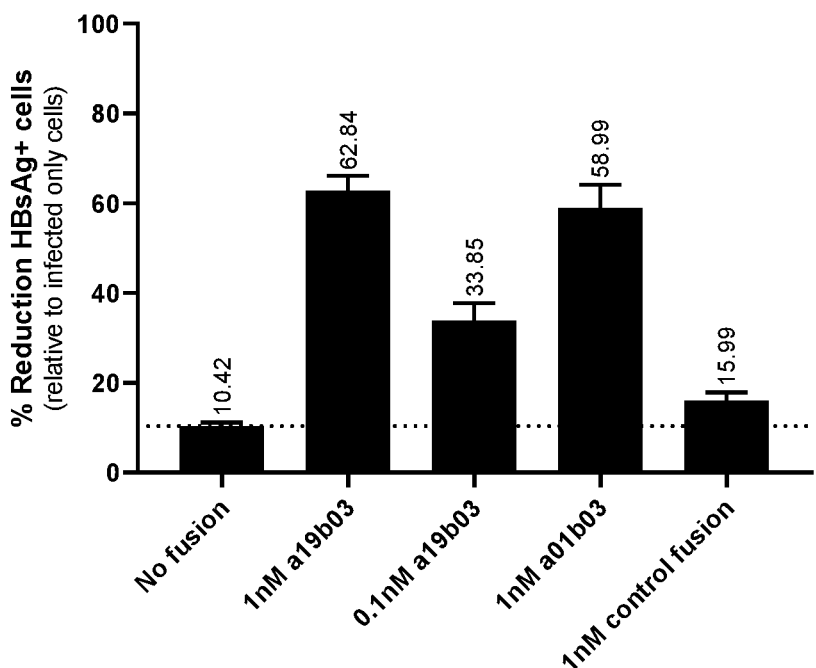
FIG. 9—provides cellular data demonstrating that TCR-
antiCD3 fusion molecules comprising the mutated TCR
variable domains as set out in FIGS. 2 and 3 mediate a
reduction in percentage of infected cells.

FIG. 9 show that both a19b03 and a01b03 TCR-antiCD3 fusions lead to an approximately 60% reduction in the % of infected cells at 1 nM fusion. The effect is titratable with 0.1 nM giving a 34% reduction.

These data indicate that fusion molecules comprising the TCR variable domains shown in FIGS. 2 and 3 can effectively clear infected cells.

---

The invention claimed is:

1. A specific binding molecule having the property of binding to a GLSPTVWLSV (SEQ ID NO: 1) HLA-A*02 complex and/or a GLSPTVWLSA (SEQ ID NO: 17) HLA-A*02 complex and comprising a T cell receptor (TCR) alpha chain variable domain and a TCR beta chain variable domain each of which comprises FR1-CDR1-FR2-CDR2-FR3-CDR3-FR4, where FR is a framework region and CDR is a complementarity determining region, wherein the specific binding molecule has one of the following combinations of TCR alpha chain variable domain CDRs and TCR beta chain variable domain CDRs:

a) TCR alpha chain variable domain CDR1, CDR2 and CDR3 sequences provided in SEQ ID NOs: 18, 19 and 25, respectively, and TCR beta chain variable domain CDR1, CDR2 and CDR3 sequences provided in SEQ ID NOs: 26, 22 and 30, respectively;

b) TCR alpha chain variable domain CDR1, CDR2 and CDR3 sequences provided in SEQ ID NOs: 18, 19 and 25, respectively, and TCR beta chain variable domain CDR1, CDR2 and CDR3 sequences provided in SEQ ID NOs: 27, 22 and 31, respectively;

c) TCR alpha chain variable domain CDR1, CDR2 and CDR3 sequences provided in SEQ ID NOs: 18, 19 and 25, respectively, and TCR beta chain variable domain CDR1, CDR2 and CDR3 sequences provided in SEQ ID NOs: 21, 22 and 32, respectively;

d) TCR alpha chain variable domain CDR1, CDR2 and CDR3 sequences provided in SEQ ID NOs: 18, 19 and 25, respectively, and TCR beta chain variable domain CDR1, CDR2 and CDR3 sequences provided in SEQ ID NOs: 21, 29 and 31, respectively;

e) TCR alpha chain variable domain CDR1, CDR2 and CDR3 sequences provided in SEQ ID NOs: 18, 19 and 25, respectively, and TCR beta chain variable domain CDR1, CDR2 and CDR3 sequences provided in SEQ ID NOs: 28, 22 and 31, respectively;

f) TCR alpha chain variable domain CDR1, CDR2 and CDR3 sequences provided in SEQ ID NOs: 18, 24 and 25, respectively, and TCR beta chain variable domain CDR1, CDR2 and CDR3 sequences provided in SEQ ID NOs: 27, 22 and 31, respectively; or g) TCR alpha chain variable domain CDR1, CDR2 and CDR3 sequences provided in SEQ ID NOs: 18, 24 and 25, respectively, and TCR beta chain variable domain CDR1, CDR2 and CDR3 sequences provided in SEQ ID NOs: 28, 22 and 31, respectively.

2. The specific binding molecule of claim 1, wherein the TCR alpha chain variable domain framework regions comprise the following sequences:

FR1—amino acids 1-26 of SEQ ID NO: 2,
FR2—amino acids 33-49 of SEQ ID NO: 2,
FR3—amino acids 56-88 of SEQ ID NO: 2, and
FR4—amino acids 102-111 of SEQ ID NO: 2,
or respective sequences having at least 90% identity to said sequences; and
the TCR beta chain variable domain framework regions comprise the following sequences:
FR1—amino acids 1-26 of SEQ ID NO: 3,
FR2—amino acids 32-48 of SEQ ID NO: 3,
FR3—amino acids 55-90 of SEQ ID NO: 3, and
FR4—amino acids 106-114 of SEQ ID NO: 3,
or respective sequences having at least 90% identity to said sequences.

3. The specific binding molecule as claimed in claim 1, wherein the TCR alpha chain variable domain and the TCR beta chain variable domain are selected from the amino acid sequences of:

a) a TCR alpha chain variable domain sequence provided in SEQ ID NO: 4 and a TCR beta chain variable domain sequence provided in SEQ ID NO: 7;

b) a TCR alpha chain variable domain sequence provided in SEQ ID NO 4 and a TCR beta chain variable domain sequence provided in SEQ ID NO: 8;

c) a TCR alpha chain variable domain sequence provided in SEQ ID NO: 4 and a TCR beta chain variable domain sequence provided in SEQ ID NO: 9;

d) a TCR alpha chain variable domain sequence provided in SEQ ID NO. 4 and a TCR beta chain variable domain sequence provided in SEQ ID NO: 10;

e) a TCR alpha chain variable domain sequence provided in SEQ ID NO: 4 and a TCR beta chain variable domain sequence provided in SEQ ID NO: 11;

f) a TCR alpha chain variable domain sequence provided in SEQ ID NO: 5 and a TCR beta chain variable domain sequence provided in SEQ ID NO: 8;

g) a TCR alpha chain variable domain sequence provided in SEQ ID NO: 5 and a TCR beta chain variable domain sequence provided in SEQ ID NO: 11; or h) a TCR alpha chain variable domain sequence provided in SEQ ID NO: 6 and a TCR beta chain variable domain sequence provided in SEQ ID NO: 8.

4. The specific binding molecule as claimed in claim 1, which is an alpha-beta heterodimer, having a TCR alpha chain TRAC constant domain sequence and a TCR beta chain TRBC1 or TRBC2 constant domain sequence.

5. The specific binding molecule as claimed in claim 4, wherein the TCR alpha chain TRAC constant domain sequence and the TCR beta chain TRBC1 or TRBC2 constant domain sequence are modified by truncation or substitution to delete a native disulfide bond between Cys4 of exon 2 of the TCR alpha chain TRAC constant domain sequence and Cys2 of exon 2 of the TCR beta chain TRBC1 or TRBC2 constant domain sequence.

6. The specific binding molecule as claimed in claim 4, wherein the TCR alpha TRAC constant domain sequence and the TCR beta chain TRBC1 or TRBC2 constant domain sequence are modified by substitution of cysteine residues for Thr 48 of TRAC and Ser 57 of TRBC1 or TRBC2, said cysteine residues forming a non-native disulfide bond between the TCR alpha chain TRAC constant domain sequence and the TCR beta TRBC1 or TRBC2 constant domain sequence.

7. The specific binding molecule as claimed in claim 1, which is in single chain format of the type Vα-L-Vβ, Vβ-L-Vα, Vα-Cα-L-Vβ, Vα-L-Vβ-Cβ, wherein Vα and Vβ are the TCR alpha (α) chain variable domain and the TCR beta (β) chain variable domain respectively, Cα and Cβ are TCR α constant domain and TCR β constant domain respectively, and L is a linker sequence.

8. The specific binding molecule as claimed in claim 1 associated with a detectable label, a therapeutic agent, or a pharmacokinetic (PK) modifying moiety.

9. The specific binding molecule as claimed in claim 8, wherein an anti-CD3 antibody is covalently linked to the C-terminus or the N-terminus of the TCR alpha chain variable domain or the TCR beta chain variable domain.

10. The specific binding molecule as claimed in claim 9, wherein the linker sequence is selected from the group consisting of GGGGS (SEQ ID NO: 33), GGGSG (SEQ ID NO: 34), GGSGG (SEQ ID NO: 35), GSGGG (SEQ ID NO: 36), GSGGGP (SEQ ID NO: 37), GGEPS (SEQ ID NO: 38), GGEGGGP (SEQ ID NO: 39), GGEGGGSEGGGS (SEQ ID NO: 40), and GGGSGGGG (SEQ ID NO: 41).

11. A specific binding molecule-anti-CD3 fusion molecule, wherein the specific binding molecule-anti-CD3 fusion molecule comprises a TCR alpha chain variable domain which comprises an amino acid sequence selected from SEQ ID NOs: 4-6 and a TCR beta chain variable domain which comprises an amino acid sequence selected from SEQ ID NOs: 7-11, and wherein an anti-CD3 antibody is covalently linked to the N-terminus or the C-terminus of the TCR beta chain variable domain via a linker sequence selected from SEQ ID NOs: 33-41.

12. The specific binding molecule-anti-CD3 fusion molecule as claimed in claim 11, comprising:

a TCR alpha chain amino acid sequence selected from SEQ ID NOs: 12, 14, and 15, or a TCR alpha chain amino acid sequence that has at least 90% identity to the amino acid sequences as set forth in SEQ ID NOs: 12, 14, or 15, and a TCR beta chain amino acid sequence selected from SEQ ID NOs: 13 and 16, or a TCR beta chain amino acid sequence that has at least 90% identity to the amino acid sequences as set forth in SEQ ID NOs: 13 or 16.

13. The specific binding molecule-anti CD3 fusion molecule as claimed in claim 12, comprising:

(a) a TCR alpha chain amino acid sequence corresponding to SEQ ID NO: 12 and a TCR beta chain amino acid sequence corresponding to SEQ ID NO: 13;

(b) a TCR alpha chain amino acid sequence corresponding to SEQ ID NO: 14 and a TCR beta chain amino acid sequence corresponding to SEQ ID NO: 13;

(c) a TCR alpha chain amino acid sequence corresponding to SEQ ID NO: 15 and a TCR beta chain amino acid sequence corresponding to SEQ ID NO: 13; or (d) a TCR alpha chain amino acid sequence corresponding to SEQ ID NO: 14 and a TCR beta chain amino acid sequence corresponding to SEQ ID NO: 16.

14. One or more nucleic acids encoding the TCR alpha chain variable domain and the TCR beta chain variable domain as claimed in claim 1.

15. An expression vector comprising the one or more nucleic acids of claim 14.

16. A cell comprising:

(a) an expression vector comprising the one or more nucleic acids of claim 14, wherein the TCR alpha chain variable domain and the TCR beta chain variable domain are encoded in a single open reading frame, or two distinct open reading frames; or (b) a first expression vector which comprises a nucleic acid encoding the TCR alpha chain variable domain as claimed in claim 14, and a second expression vector which comprises a nucleic acid encoding the TCR beta chain variable domain as claimed in claim 14.

17. An engineered cell presenting the specific binding molecule as claimed in claim 1.

18. A pharmaceutical composition comprising the specific binding molecule of claim 1, together with one or more pharmaceutically acceptable carriers or excipients.

19. A method of treating a subject having chronic hepatitis B virus (HBV) infection or a cancer or tumor resulting from chronic HBV infection comprising administering to the subject in need thereof a pharmaceutically effective dose of the pharmaceutical composition according to claim 18.

20. A method of producing a specific binding molecule comprising:

a) introducing one or more nucleic acids encoding the TCR alpha chain variable domain and the TCR beta chain variable domain of the specific binding molecule as claimed in claim 1 into a cell, b) maintaining the cell under conditions for expression of the TCR alpha chain variable domain and the TCR beta chain variable domain of the specific binding molecule, and c) isolating the specific binding molecule.

\* \* \* \* \*

SEQUENCE LISTING

```
<160> NUMBER OF SEQ ID NOS: 51

<210> SEQ ID NO 1
<211> LENGTH: 10
<212> TYPE: PRT
<213> ORGANISM: Homo sapiens

<400> SEQUENCE: 1

Gly Leu Ser Pro Thr Val Trp Leu Ser Val
1               5               10

<210> SEQ ID NO 2
<211> LENGTH: 197
<212> TYPE: PRT
<213> ORGANISM: Artificial sequence
<220> FEATURE:
<223> OTHER INFORMATION: Amino acid sequence of the scaffold alpha chain
      extracellular region

<400> SEQUENCE: 2

Ala Lys Glu Val Glu Gln Asn Ser Gly Pro Leu Ser Val Pro Glu Gly
1               5                   10                  15

Ala Ile Ala Ser Leu Asn Cys Thr Tyr Ser Asp Arg Gly Ser Gln Ser
            20                  25                  30

Phe Phe Trp Tyr Arg Gln Tyr Ser Gly Lys Ser Pro Glu Leu Ile Met
        35                  40                  45

Ser Ile Tyr Ser Asn Gly Asp Lys Glu Asp Gly Arg Phe Thr Ala Gln
    50                  55                  60

Leu Asn Lys Ala Ser Gln Tyr Val Ser Leu Leu Ile Arg Asp Ser Gln
65                  70                  75                  80
```

-continued

Pro Ser Asp Ser Ala Thr Tyr Leu Cys Ala Val Arg Asn Tyr Asn Thr
                85                  90                  95

Asp Lys Leu Ile Phe Gly Thr Gly Thr Arg Leu Gln Val Phe Pro Asn
            100                 105                 110

Ile Gln Asn Pro Asp Pro Ala Val Tyr Gln Leu Arg Asp Ser Lys Ser
            115                 120                 125

Ser Asp Lys Ser Val Cys Leu Phe Thr Asp Phe Asp Ser Gln Thr Asn
    130                 135                 140

Val Ser Gln Ser Lys Asp Ser Asp Val Tyr Ile Thr Asp Lys Cys Val
145                 150                 155                 160

Leu Asp Met Arg Ser Met Asp Phe Lys Ser Asn Ser Ala Val Ala Trp
                165                 170                 175

Ser Asn Lys Ser Asp Phe Ala Cys Ala Asn Ala Phe Asn Asn Ser Ile
            180                 185                 190

Ile Pro Glu Asp Thr
            195

<210> SEQ ID NO 3
<211> LENGTH: 244
<212> TYPE: PRT
<213> ORGANISM: Artificial sequence
<220> FEATURE:
<223> OTHER INFORMATION: Amino acid sequence of the scaffold beta chain
      extracellular region

<400> SEQUENCE: 3

Asn Ala Gly Val Thr Gln Thr Pro Lys Phe Gln Val Leu Lys Thr Gly
1               5                   10                  15

Gln Ser Met Thr Leu Gln Cys Ala Gln Asp Met Asn His Glu Tyr Met
                20                  25                  30

Ser Trp Tyr Arg Gln Asp Pro Gly Met Gly Leu Arg Leu Ile His Tyr
            35                  40                  45

Ser Val Gly Ala Gly Ile Thr Asp Gln Gly Glu Val Pro Asn Gly Tyr
    50                  55                  60

Asn Val Ser Arg Ser Thr Thr Glu Asp Phe Pro Leu Arg Leu Leu Ser
65                  70                  75                  80

Ala Ala Pro Ser Gln Thr Ser Val Tyr Phe Cys Ala Ser Ser Tyr Ala
                85                  90                  95

Thr Gly Gly Thr Gly Glu Leu Phe Phe Gly Glu Gly Ser Arg Leu Thr
            100                 105                 110

Val Leu Glu Asp Leu Lys Asn Val Phe Pro Pro Glu Val Ala Val Phe
            115                 120                 125

Glu Pro Ser Glu Ala Glu Ile Ser His Thr Gln Lys Ala Thr Leu Val
    130                 135                 140

Cys Leu Ala Thr Gly Phe Tyr Pro Asp His Val Glu Leu Ser Trp Trp
145                 150                 155                 160

Val Asn Gly Lys Glu Val His Ser Gly Val Cys Thr Asp Pro Gln Pro
                165                 170                 175

Leu Lys Glu Gln Pro Ala Leu Asn Asp Ser Arg Tyr Ala Leu Ser Ser
            180                 185                 190

Arg Leu Arg Val Ser Ala Thr Phe Trp Gln Asp Pro Arg Asn His Phe
            195                 200                 205

Arg Cys Gln Val Gln Phe Tyr Gly Leu Ser Glu Asn Asp Glu Trp Thr
    210                 215                 220

Gln Asp Arg Ala Lys Pro Val Thr Gln Ile Val Ser Ala Glu Ala Trp
225                 230                 235                 240

```
Gly Arg Ala Asp

<210> SEQ ID NO 4
<211> LENGTH: 111
<212> TYPE: PRT
<213> ORGANISM: Artificial sequence
<220> FEATURE:
<223> OTHER INFORMATION: mutant alpha chain variable region (a01)

<400> SEQUENCE: 4

Ala Lys Glu Val Glu Gln Asn Ser Gly Pro Leu Ser Val Pro Glu Gly
1               5                   10                  15

Ala Ile Ala Ser Leu Asn Cys Thr Tyr Ser Asp Arg Gly Ser Gln Ser
            20                  25                  30

Phe Phe Trp Tyr Arg Gln Tyr Ser Gly Lys Ser Pro Glu Leu Ile Met
        35                  40                  45

Ser Ile Tyr Ser Asn Gly Asp Lys Glu Asp Gly Arg Phe Thr Ala Gln
    50                  55                  60

Leu Asn Lys Ala Ser Gln Tyr Val Ser Leu Leu Ile Arg Asp Ser Gln
65                  70                  75                  80

Pro Ser Asp Ser Ala Thr Tyr Leu Cys Ala Ala Arg Asn Tyr Lys Thr
                85                  90                  95

Asp Leu Leu Ile Phe Gly Thr Gly Thr Arg Leu Gln Val Phe Pro
            100                 105                 110

<210> SEQ ID NO 5
<211> LENGTH: 111
<212> TYPE: PRT
<213> ORGANISM: Artificial sequence
<220> FEATURE:
<223> OTHER INFORMATION: mutant alpha chain variable region (a13)

<400> SEQUENCE: 5

Ala Lys Glu Val Glu Gln Asn Ser Gly Pro Leu Ser Val Pro Glu Gly
1               5                   10                  15

Ala Ile Ala Ser Leu Asn Cys Thr Tyr Ser Asp Arg Gly Ser Gln Ser
            20                  25                  30

Phe Phe Trp Tyr Arg Gln Tyr Ser Gly Lys Ser Pro Glu Leu Ile Met
        35                  40                  45

Ser Ile Tyr Ser Asp Gly Asp Lys Glu Asp Gly Arg Phe Thr Ala Gln
    50                  55                  60

Leu Asn Lys Ala Ser Gln Tyr Val Ser Leu Leu Ile Arg Asp Ser Gln
65                  70                  75                  80

Pro Ser Asp Ser Ala Thr Tyr Leu Cys Ala Ala Arg Asn Tyr Lys Thr
                85                  90                  95

Asp Leu Leu Ile Phe Gly Thr Gly Thr Arg Leu Gln Val Phe Pro
            100                 105                 110

<210> SEQ ID NO 6
<211> LENGTH: 111
<212> TYPE: PRT
<213> ORGANISM: Artificial sequence
<220> FEATURE:
<223> OTHER INFORMATION: mutant alpha chain variable region (a19)

<400> SEQUENCE: 6

Ala Lys Glu Val Glu Gln Asn Ser Gly Pro Leu Ser Val Pro Glu Gly
1               5                   10                  15

Ala Ile Ala Ser Leu Asn Cys Thr Tyr Ser Asp Arg Gly Ser Gln Ser
```

```
                   20               25               30

Phe Phe Trp Tyr Arg Gln Tyr Ser Gly Lys Gly Pro Glu Leu Ile Met
        35               40               45

Ser Ile Tyr Ser Asp Gly Asp Lys Glu Asp Gly Arg Phe Thr Ala Gln
    50               55               60

Leu Asn Lys Ala Ser Gln Tyr Val Ser Leu Leu Ile Arg Asp Ser Gln
65               70               75               80

Pro Ser Asp Ser Ala Thr Tyr Leu Cys Ala Ala Arg Asn Tyr Lys Thr
                85               90               95

Asp Leu Leu Ile Phe Gly Thr Gly Thr Arg Leu Gln Val Phe Pro
                100              105              110

<210> SEQ ID NO 7
<211> LENGTH: 114
<212> TYPE: PRT
<213> ORGANISM: Artificial sequence
<220> FEATURE:
<223> OTHER INFORMATION: mutant beta chain variable region (b02)

<400> SEQUENCE: 7

Asn Ala Gly Val Thr Gln Thr Pro Lys Phe Gln Val Leu Lys Thr Gly
1               5               10               15

Gln Ser Met Thr Leu Gln Cys Ala Gln Asp Leu Asn His Gly Tyr Met
            20               25               30

Ser Trp Tyr Arg Gln Asp Pro Gly Met Gly Leu Arg Leu Ile His Tyr
        35               40               45

Ser Val Gly Ala Gly Ile Thr Asp Gln Gly Glu Val Pro Asn Gly Tyr
    50               55               60

Asn Val Ser Arg Ser Thr Thr Glu Asp Phe Pro Leu Arg Leu Leu Ser
65               70               75               80

Ala Ala Pro Ser Gln Thr Ser Val Tyr Phe Cys Ala Ser Ser Tyr Ala
                85               90               95

Thr Gly Gly Thr Gly Val Leu Phe Phe Gly Glu Gly Ser Arg Leu Thr
                100              105              110

Val Leu

<210> SEQ ID NO 8
<211> LENGTH: 114
<212> TYPE: PRT
<213> ORGANISM: Artificial sequence
<220> FEATURE:
<223> OTHER INFORMATION: mutant beta chain variable region (b03)

<400> SEQUENCE: 8

Asn Ala Gly Val Thr Gln Thr Pro Lys Phe Gln Val Leu Lys Thr Gly
1               5               10               15

Gln Ser Met Thr Leu Gln Cys Ala Gln Asp Met Ser His Gly Tyr Met
            20               25               30

Ser Trp Tyr Arg Gln Asp Pro Gly Met Gly Leu Arg Leu Ile His Tyr
        35               40               45

Ser Val Gly Ala Gly Ile Thr Asp Gln Gly Glu Val Pro Asn Gly Tyr
    50               55               60

Asn Val Ser Arg Ser Thr Thr Glu Asp Phe Pro Leu Arg Leu Leu Ser
65               70               75               80

Ala Ala Pro Ser Gln Thr Ser Val Tyr Phe Cys Ala Ser Ser Tyr Ala
                85               90               95

Thr Gly Gly Thr Gly Asp Leu Phe Phe Gly Glu Gly Ser Arg Leu Thr
```

```
                100                 105                 110

Val Leu

<210> SEQ ID NO 9
<211> LENGTH: 114
<212> TYPE: PRT
<213> ORGANISM: Artificial sequence
<220> FEATURE:
<223> OTHER INFORMATION: mutant beta chain variable region (b04)

<400> SEQUENCE: 9

Asn Ala Gly Val Thr Gln Thr Pro Lys Phe Gln Val Leu Lys Thr Gly
1               5                   10                  15

Gln Ser Met Thr Leu Gln Cys Ala Gln Asp Met Asn His Glu Tyr Met
            20                  25                  30

Ser Trp Tyr Arg Gln Asp Pro Gly Met Gly Leu Arg Leu Ile His Tyr
        35                  40                  45

Ser Val Gly Ala Gly Ile Thr Asp Gln Gly Glu Val Pro Asn Gly Tyr
    50                  55                  60

Asn Val Ser Arg Ser Thr Thr Glu Asp Phe Pro Leu Arg Leu Leu Ser
65                  70                  75                  80

Ala Ala Pro Ser Gln Thr Ser Val Tyr Phe Cys Ala Ser Ser Tyr Ala
                85                  90                  95

Thr Gly Gly Thr Gly Leu Leu Phe Phe Gly Glu Gly Ser Arg Leu Thr
            100                 105                 110

Val Leu

<210> SEQ ID NO 10
<211> LENGTH: 114
<212> TYPE: PRT
<213> ORGANISM: Artificial sequence
<220> FEATURE:
<223> OTHER INFORMATION: mutant beta chain variable region (b05)

<400> SEQUENCE: 10

Asn Ala Gly Val Thr Gln Thr Pro Lys Phe Gln Val Leu Lys Thr Gly
1               5                   10                  15

Gln Ser Met Thr Leu Gln Cys Ala Gln Asp Met Asn His Glu Tyr Met
            20                  25                  30

Ser Trp Tyr Arg Gln Asp Pro Gly Met Gly Leu Arg Leu Ile His Tyr
        35                  40                  45

Ser Leu Gly Ala Gly Ile Thr Asp Gln Gly Glu Val Pro Asn Gly Tyr
    50                  55                  60

Asn Val Ser Arg Ser Thr Thr Glu Asp Phe Pro Leu Arg Leu Leu Ser
65                  70                  75                  80

Ala Ala Pro Ser Gln Thr Ser Val Tyr Phe Cys Ala Ser Ser Tyr Ala
                85                  90                  95

Thr Gly Gly Thr Gly Asp Leu Phe Phe Gly Glu Gly Ser Arg Leu Thr
            100                 105                 110

Val Leu

<210> SEQ ID NO 11
<211> LENGTH: 114
<212> TYPE: PRT
<213> ORGANISM: Artificial sequence
<220> FEATURE:
<223> OTHER INFORMATION: mutant beta chain variable region (b09)

<400> SEQUENCE: 11
```

```
Asn Ala Gly Val Thr Gln Thr Pro Lys Phe Gln Val Leu Lys Thr Gly
1               5                   10                  15

Gln Ser Met Thr Leu Gln Cys Ala Gln Asp Leu Ser His Gly Tyr Met
            20                  25                  30

Ser Trp Tyr Arg Gln Asp Pro Gly Met Gly Leu Arg Leu Ile His Tyr
        35                  40                  45

Ser Val Gly Ala Gly Ile Thr Asp Gln Gly Glu Val Pro Asn Gly Tyr
    50                  55                  60

Asn Val Ser Arg Ser Thr Thr Glu Asp Phe Pro Leu Arg Leu Leu Ser
65                  70                  75                  80

Ala Ala Pro Ser Gln Thr Ser Val Tyr Phe Cys Ala Ser Ser Tyr Ala
                85                  90                  95

Thr Gly Gly Thr Gly Asp Leu Phe Phe Gly Glu Gly Ser Arg Leu Thr
            100                 105                 110

Val Leu
```

```
<210> SEQ ID NO 12
<211> LENGTH: 197
<212> TYPE: PRT
<213> ORGANISM: Artificial sequence
<220> FEATURE:
<223> OTHER INFORMATION: alpha chain (a19)

<400> SEQUENCE: 12
```

```
Ala Lys Glu Val Glu Gln Asn Ser Gly Pro Leu Ser Val Pro Glu Gly
1               5                   10                  15

Ala Ile Ala Ser Leu Asn Cys Thr Tyr Ser Asp Arg Gly Ser Gln Ser
            20                  25                  30

Phe Phe Trp Tyr Arg Gln Tyr Ser Gly Lys Gly Pro Glu Leu Ile Met
        35                  40                  45

Ser Ile Tyr Ser Asp Gly Asp Lys Glu Asp Gly Arg Phe Thr Ala Gln
    50                  55                  60

Leu Asn Lys Ala Ser Gln Tyr Val Ser Leu Leu Ile Arg Asp Ser Gln
65                  70                  75                  80

Pro Ser Asp Ser Ala Thr Tyr Leu Cys Ala Ala Arg Asn Tyr Lys Thr
                85                  90                  95

Asp Leu Leu Ile Phe Gly Thr Gly Thr Arg Leu Gln Val Phe Pro Asn
            100                 105                 110

Ile Gln Asn Pro Asp Pro Ala Val Tyr Gln Leu Arg Asp Ser Lys Ser
        115                 120                 125

Ser Asp Lys Ser Val Cys Leu Phe Thr Asp Phe Asp Ser Gln Thr Asn
        130                 135                 140

Val Ser Gln Ser Lys Asp Ser Asp Val Tyr Ile Thr Asp Lys Cys Val
145                 150                 155                 160

Leu Asp Met Arg Ser Met Asp Phe Lys Ser Asn Ser Ala Val Ala Trp
            165                 170                 175

Ser Asn Lys Ser Asp Phe Ala Cys Ala Asn Ala Phe Asn Asn Ser Ile
            180                 185                 190

Ile Pro Glu Asp Thr
        195
```

```
<210> SEQ ID NO 13
<211> LENGTH: 502
<212> TYPE: PRT
<213> ORGANISM: Artificial sequence
<220> FEATURE:
```

-continued

<223> OTHER INFORMATION: beta chain (b03)

<400> SEQUENCE: 13

```
Ala Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Arg Asn Tyr
            20                  25                  30

Leu Asn Trp Tyr Gln Gln Lys Pro Gly Lys Ala Pro Lys Leu Leu Ile
        35                  40                  45

Tyr Tyr Thr Ser Arg Leu Glu Ser Gly Val Pro Ser Arg Phe Ser Gly
    50                  55                  60

Ser Gly Ser Gly Thr Asp Tyr Thr Leu Thr Ile Ser Ser Leu Gln Pro
65                  70                  75                  80

Glu Asp Phe Ala Thr Tyr Tyr Cys Gln Gln Gly Asn Thr Leu Pro Trp
            85                  90                  95

Thr Phe Gly Gln Gly Thr Lys Val Glu Ile Lys Gly Gly Gly Gly Ser
            100                 105                 110

Gly Gly Gly Gly Ser Gly Gly Gly Ser Gly Gly Gly Gly Ser Gly
        115                 120                 125

Gly Gly Ser Glu Val Gln Leu Val Glu Ser Gly Gly Gly Leu Val Gln
    130                 135                 140

Pro Gly Gly Ser Leu Arg Leu Ser Cys Ala Ala Ser Gly Tyr Ser Phe
145                 150                 155                 160

Thr Gly Tyr Thr Met Asn Trp Val Arg Gln Ala Pro Gly Lys Gly Leu
            165                 170                 175

Glu Trp Val Ala Leu Ile Asn Pro Tyr Lys Gly Val Ser Thr Tyr Asn
            180                 185                 190

Gln Lys Phe Lys Asp Arg Phe Thr Ile Ser Val Asp Lys Ser Lys Asn
        195                 200                 205

Thr Ala Tyr Leu Gln Met Asn Ser Leu Arg Ala Glu Asp Thr Ala Val
    210                 215                 220

Tyr Tyr Cys Ala Arg Ser Gly Tyr Tyr Gly Asp Ser Asp Trp Tyr Phe
225                 230                 235                 240

Asp Val Trp Gly Gln Gly Thr Leu Val Thr Val Ser Ser Gly Gly Gly
            245                 250                 255

Gly Ser Asn Ala Gly Val Thr Gln Thr Pro Lys Phe Gln Val Leu Lys
        260                 265                 270

Thr Gly Gln Ser Met Thr Leu Gln Cys Ala Gln Asp Met Ser His Gly
        275                 280                 285

Tyr Met Ser Trp Tyr Arg Gln Asp Pro Gly Met Gly Leu Arg Leu Ile
    290                 295                 300

His Tyr Ser Val Gly Ala Gly Ile Thr Asp Gln Gly Glu Val Pro Asn
305                 310                 315                 320

Gly Tyr Asn Val Ser Arg Ser Thr Thr Glu Asp Phe Pro Leu Arg Leu
            325                 330                 335

Leu Ser Ala Ala Pro Ser Gln Thr Ser Val Tyr Phe Cys Ala Ser Ser
            340                 345                 350

Tyr Ala Thr Gly Gly Thr Gly Asp Leu Phe Phe Gly Glu Gly Ser Arg
        355                 360                 365

Leu Thr Val Leu Glu Asp Leu Lys Asn Val Phe Pro Pro Glu Val Ala
    370                 375                 380

Val Phe Glu Pro Ser Glu Ala Glu Ile Ser His Thr Gln Lys Ala Thr
385                 390                 395                 400
```

-continued

```
Leu Val Cys Leu Ala Thr Gly Phe Tyr Pro Asp His Val Glu Leu Ser
            405                 410                 415

Trp Trp Val Asn Gly Lys Glu Val His Ser Gly Val Cys Thr Asp Pro
            420                 425                 430

Gln Pro Leu Lys Glu Gln Pro Ala Leu Asn Asp Ser Arg Tyr Ala Leu
            435                 440                 445

Ser Ser Arg Leu Arg Val Ser Ala Thr Phe Trp Gln Asp Pro Arg Asn
    450                 455                 460

His Phe Arg Cys Gln Val Gln Phe Tyr Gly Leu Ser Glu Asn Asp Glu
465                 470                 475                 480

Trp Thr Gln Asp Arg Ala Lys Pro Val Thr Gln Ile Val Ser Ala Glu
            485                 490                 495

Ala Trp Gly Arg Ala Asp
            500
```

```
<210> SEQ ID NO 14
<211> LENGTH: 197
<212> TYPE: PRT
<213> ORGANISM: Artificial sequence
<220> FEATURE:
<223> OTHER INFORMATION: alpha chain (a13)

<400> SEQUENCE: 14
```

```
Ala Lys Glu Val Glu Gln Asn Ser Gly Pro Leu Ser Val Pro Glu Gly
1               5                   10                  15

Ala Ile Ala Ser Leu Asn Cys Thr Tyr Ser Asp Arg Gly Ser Gln Ser
            20                  25                  30

Phe Phe Trp Tyr Arg Gln Tyr Ser Gly Lys Ser Pro Glu Leu Ile Met
            35                  40                  45

Ser Ile Tyr Ser Asp Gly Asp Lys Glu Asp Gly Arg Phe Thr Ala Gln
    50                  55                  60

Leu Asn Lys Ala Ser Gln Tyr Val Ser Leu Leu Ile Arg Asp Ser Gln
65                  70                  75                  80

Pro Ser Asp Ser Ala Thr Tyr Leu Cys Ala Ala Arg Asn Tyr Lys Thr
            85                  90                  95

Asp Leu Leu Ile Phe Gly Thr Gly Thr Arg Leu Gln Val Phe Pro Asn
            100                 105                 110

Ile Gln Asn Pro Asp Pro Ala Val Tyr Gln Leu Arg Asp Ser Lys Ser
            115                 120                 125

Ser Asp Lys Ser Val Cys Leu Phe Thr Asp Phe Asp Ser Gln Thr Asn
    130                 135                 140

Val Ser Gln Ser Lys Asp Ser Asp Val Tyr Ile Thr Asp Lys Cys Val
145                 150                 155                 160

Leu Asp Met Arg Ser Met Asp Phe Lys Ser Asn Ser Ala Val Ala Trp
            165                 170                 175

Ser Asn Lys Ser Asp Phe Ala Cys Ala Asn Ala Phe Asn Asn Ser Ile
            180                 185                 190

Ile Pro Glu Asp Thr
            195
```

```
<210> SEQ ID NO 15
<211> LENGTH: 197
<212> TYPE: PRT
<213> ORGANISM: Artificial sequence
<220> FEATURE:
<223> OTHER INFORMATION: alpha chain (a01)

<400> SEQUENCE: 15
```

-continued

```
Ala Lys Glu Val Glu Gln Asn Ser Gly Pro Leu Ser Val Pro Glu Gly
1               5                   10                  15

Ala Ile Ala Ser Leu Asn Cys Thr Tyr Ser Asp Arg Gly Ser Gln Ser
            20                  25                  30

Phe Phe Trp Tyr Arg Gln Tyr Ser Gly Lys Ser Pro Glu Leu Ile Met
        35                  40                  45

Ser Ile Tyr Ser Asn Gly Asp Lys Glu Asp Gly Arg Phe Thr Ala Gln
    50                  55                  60

Leu Asn Lys Ala Ser Gln Tyr Val Ser Leu Leu Ile Arg Asp Ser Gln
65                  70                  75                  80

Pro Ser Asp Ser Ala Thr Tyr Leu Cys Ala Ala Arg Asn Tyr Lys Thr
                85                  90                  95

Asp Leu Leu Ile Phe Gly Thr Gly Thr Arg Leu Gln Val Phe Pro Asn
            100                 105                 110

Ile Gln Asn Pro Asp Pro Ala Val Tyr Gln Leu Arg Asp Ser Lys Ser
            115                 120                 125

Ser Asp Lys Ser Val Cys Leu Phe Thr Asp Phe Asp Ser Gln Thr Asn
    130                 135                 140

Val Ser Gln Ser Lys Asp Ser Asp Val Tyr Ile Thr Asp Lys Cys Val
145                 150                 155                 160

Leu Asp Met Arg Ser Met Asp Phe Lys Ser Asn Ser Ala Val Ala Trp
            165                 170                 175

Ser Asn Lys Ser Asp Phe Ala Cys Ala Asn Ala Phe Asn Asn Ser Ile
            180                 185                 190

Ile Pro Glu Asp Thr
            195
```

```
<210> SEQ ID NO 16
<211> LENGTH: 502
<212> TYPE: PRT
<213> ORGANISM: Artificial sequence
<220> FEATURE:
<223> OTHER INFORMATION: beta chain (b09)

<400> SEQUENCE: 16
```

```
Ala Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Arg Asn Tyr
            20                  25                  30

Leu Asn Trp Tyr Gln Gln Lys Pro Gly Lys Ala Pro Lys Leu Leu Ile
        35                  40                  45

Tyr Tyr Thr Ser Arg Leu Glu Ser Gly Val Pro Ser Arg Phe Ser Gly
    50                  55                  60

Ser Gly Ser Gly Thr Asp Tyr Thr Leu Thr Ile Ser Ser Leu Gln Pro
65                  70                  75                  80

Glu Asp Phe Ala Thr Tyr Tyr Cys Gln Gln Gly Asn Thr Leu Pro Trp
                85                  90                  95

Thr Phe Gly Gln Gly Thr Lys Val Glu Ile Lys Gly Gly Gly Gly Ser
            100                 105                 110

Gly Gly Gly Gly Ser Gly Gly Gly Ser Gly Gly Gly Gly Ser Gly
            115                 120                 125

Gly Gly Ser Glu Val Gln Leu Val Glu Ser Gly Gly Gly Leu Val Gln
    130                 135                 140

Pro Gly Gly Ser Leu Arg Leu Ser Cys Ala Ala Ser Gly Tyr Ser Phe
145                 150                 155                 160
```

-continued

```
Thr Gly Tyr Thr Met Asn Trp Val Arg Gln Ala Pro Gly Lys Gly Leu
            165                 170                 175

Glu Trp Val Ala Leu Ile Asn Pro Tyr Lys Gly Val Ser Thr Tyr Asn
            180                 185                 190

Gln Lys Phe Lys Asp Arg Phe Thr Ile Ser Val Asp Lys Ser Lys Asn
        195                 200                 205

Thr Ala Tyr Leu Gln Met Asn Ser Leu Arg Ala Glu Asp Thr Ala Val
        210                 215                 220

Tyr Tyr Cys Ala Arg Ser Gly Tyr Tyr Gly Asp Ser Asp Trp Tyr Phe
225                 230                 235                 240

Asp Val Trp Gly Gln Gly Thr Leu Val Thr Val Ser Ser Gly Gly Gly
            245                 250                 255

Gly Ser Asn Ala Gly Val Thr Gln Thr Pro Lys Phe Gln Val Leu Lys
            260                 265                 270

Thr Gly Gln Ser Met Thr Leu Gln Cys Ala Gln Asp Leu Ser His Gly
        275                 280                 285

Tyr Met Ser Trp Tyr Arg Gln Asp Pro Gly Met Gly Leu Arg Leu Ile
        290                 295                 300

His Tyr Ser Val Gly Ala Gly Ile Thr Asp Gln Gly Glu Val Pro Asn
305                 310                 315                 320

Gly Tyr Asn Val Ser Arg Ser Thr Thr Glu Asp Phe Pro Leu Arg Leu
            325                 330                 335

Leu Ser Ala Ala Pro Ser Gln Thr Ser Val Tyr Phe Cys Ala Ser Ser
            340                 345                 350

Tyr Ala Thr Gly Gly Thr Gly Asp Leu Phe Phe Gly Glu Gly Ser Arg
        355                 360                 365

Leu Thr Val Leu Glu Asp Leu Lys Asn Val Phe Pro Pro Glu Val Ala
        370                 375                 380

Val Phe Glu Pro Ser Glu Ala Glu Ile Ser His Thr Gln Lys Ala Thr
385                 390                 395                 400

Leu Val Cys Leu Ala Thr Gly Phe Tyr Pro Asp His Val Glu Leu Ser
            405                 410                 415

Trp Trp Val Asn Gly Lys Glu Val His Ser Gly Val Cys Thr Asp Pro
            420                 425                 430

Gln Pro Leu Lys Glu Gln Pro Ala Leu Asn Asp Ser Arg Tyr Ala Leu
        435                 440                 445

Ser Ser Arg Leu Arg Val Ser Ala Thr Phe Trp Gln Asp Pro Arg Asn
        450                 455                 460

His Phe Arg Cys Gln Val Gln Phe Tyr Gly Leu Ser Glu Asn Asp Glu
465                 470                 475                 480

Trp Thr Gln Asp Arg Ala Lys Pro Val Thr Gln Ile Val Ser Ala Glu
            485                 490                 495

Ala Trp Gly Arg Ala Asp
            500

<210> SEQ ID NO 17
<211> LENGTH: 10
<212> TYPE: PRT
<213> ORGANISM: Homo sapiens

<400> SEQUENCE: 17

Gly Leu Ser Pro Thr Val Trp Leu Ser Ala
1               5                   10
```

-continued

```
<210> SEQ ID NO 18
<211> LENGTH: 6
<212> TYPE: PRT
<213> ORGANISM: Artificial sequence
<220> FEATURE:
<223> OTHER INFORMATION: alpha chain CDR1

<400> SEQUENCE: 18

Asp Arg Gly Ser Gln Ser
1               5

<210> SEQ ID NO 19
<211> LENGTH: 6
<212> TYPE: PRT
<213> ORGANISM: Artificial sequence
<220> FEATURE:
<223> OTHER INFORMATION: alpha chain CDR2

<400> SEQUENCE: 19

Ile Tyr Ser Asn Gly Asp
1               5

<210> SEQ ID NO 20
<211> LENGTH: 13
<212> TYPE: PRT
<213> ORGANISM: Artificial sequence
<220> FEATURE:
<223> OTHER INFORMATION: alpha chain CDR3

<400> SEQUENCE: 20

Cys Ala Val Arg Asn Tyr Asn Thr Asp Lys Leu Ile Phe
1               5                   10

<210> SEQ ID NO 21
<211> LENGTH: 5
<212> TYPE: PRT
<213> ORGANISM: Artificial sequence
<220> FEATURE:
<223> OTHER INFORMATION: beta chain CDR1

<400> SEQUENCE: 21

Met Asn His Glu Tyr
1               5

<210> SEQ ID NO 22
<211> LENGTH: 6
<212> TYPE: PRT
<213> ORGANISM: Artificial sequence
<220> FEATURE:
<223> OTHER INFORMATION: beta chain CDR2

<400> SEQUENCE: 22

Ser Val Gly Ala Gly Ile
1               5

<210> SEQ ID NO 23
<211> LENGTH: 15
<212> TYPE: PRT
<213> ORGANISM: Artificial sequence
<220> FEATURE:
<223> OTHER INFORMATION: beta chain CDR3

<400> SEQUENCE: 23

Cys Ala Ser Ser Tyr Ala Thr Gly Gly Thr Gly Glu Leu Phe Phe
1               5                   10                  15

<210> SEQ ID NO 24
```

```
<211> LENGTH: 6
<212> TYPE: PRT
<213> ORGANISM: Artificial sequence
<220> FEATURE:
<223> OTHER INFORMATION: alpha chain CDR2

<400> SEQUENCE: 24

Ile Tyr Ser Asp Gly Asp
1               5

<210> SEQ ID NO 25
<211> LENGTH: 13
<212> TYPE: PRT
<213> ORGANISM: Artificial sequence
<220> FEATURE:
<223> OTHER INFORMATION: alpha chain CDR3

<400> SEQUENCE: 25

Cys Ala Ala Arg Asn Tyr Lys Thr Asp Leu Leu Ile Phe
1               5                   10

<210> SEQ ID NO 26
<211> LENGTH: 5
<212> TYPE: PRT
<213> ORGANISM: Artificial sequence
<220> FEATURE:
<223> OTHER INFORMATION: beta chain CDR1

<400> SEQUENCE: 26

Leu Asn His Gly Tyr
1               5

<210> SEQ ID NO 27
<211> LENGTH: 5
<212> TYPE: PRT
<213> ORGANISM: Artificial sequence
<220> FEATURE:
<223> OTHER INFORMATION: beta chain CDR1

<400> SEQUENCE: 27

Met Ser His Gly Tyr
1               5

<210> SEQ ID NO 28
<211> LENGTH: 5
<212> TYPE: PRT
<213> ORGANISM: Artificial sequence
<220> FEATURE:
<223> OTHER INFORMATION: beta chain CDR1

<400> SEQUENCE: 28

Leu Ser His Gly Tyr
1               5

<210> SEQ ID NO 29
<211> LENGTH: 6
<212> TYPE: PRT
<213> ORGANISM: Artificial sequence
<220> FEATURE:
<223> OTHER INFORMATION: beta chain CDR2

<400> SEQUENCE: 29

Ser Leu Gly Ala Gly Ile
1               5

<210> SEQ ID NO 30
<211> LENGTH: 15
```

-continued

```
<212> TYPE: PRT
<213> ORGANISM: Artificial sequence
<220> FEATURE:
<223> OTHER INFORMATION: beta chain CDR3

<400> SEQUENCE: 30

Cys Ala Ser Ser Tyr Ala Thr Gly Gly Thr Gly Val Leu Phe Phe
1               5                   10                  15

<210> SEQ ID NO 31
<211> LENGTH: 15
<212> TYPE: PRT
<213> ORGANISM: Artificial sequence
<220> FEATURE:
<223> OTHER INFORMATION: beta chain CDR3

<400> SEQUENCE: 31

Cys Ala Ser Ser Tyr Ala Thr Gly Gly Thr Gly Asp Leu Phe Phe
1               5                   10                  15

<210> SEQ ID NO 32
<211> LENGTH: 15
<212> TYPE: PRT
<213> ORGANISM: Artificial sequence
<220> FEATURE:
<223> OTHER INFORMATION: beta chain CDR3

<400> SEQUENCE: 32

Cys Ala Ser Ser Tyr Ala Thr Gly Gly Thr Gly Leu Leu Phe Phe
1               5                   10                  15

<210> SEQ ID NO 33
<211> LENGTH: 5
<212> TYPE: PRT
<213> ORGANISM: Artificial sequence
<220> FEATURE:
<223> OTHER INFORMATION: Linker

<400> SEQUENCE: 33

Gly Gly Gly Gly Ser
1               5

<210> SEQ ID NO 34
<211> LENGTH: 5
<212> TYPE: PRT
<213> ORGANISM: Artificial sequence
<220> FEATURE:
<223> OTHER INFORMATION: Linker

<400> SEQUENCE: 34

Gly Gly Gly Ser Gly
1               5

<210> SEQ ID NO 35
<211> LENGTH: 5
<212> TYPE: PRT
<213> ORGANISM: Artificial sequence
<220> FEATURE:
<223> OTHER INFORMATION: Linker

<400> SEQUENCE: 35

Gly Gly Ser Gly Gly
1               5

<210> SEQ ID NO 36
<211> LENGTH: 5
<212> TYPE: PRT
```

```
<213> ORGANISM: Artificial sequence
<220> FEATURE:
<223> OTHER INFORMATION: Linker

<400> SEQUENCE: 36

Gly Ser Gly Gly Gly
1               5

<210> SEQ ID NO 37
<211> LENGTH: 6
<212> TYPE: PRT
<213> ORGANISM: Artificial sequence
<220> FEATURE:
<223> OTHER INFORMATION: Linker

<400> SEQUENCE: 37

Gly Ser Gly Gly Gly Pro
1               5

<210> SEQ ID NO 38
<211> LENGTH: 5
<212> TYPE: PRT
<213> ORGANISM: Artificial sequence
<220> FEATURE:
<223> OTHER INFORMATION: Linker

<400> SEQUENCE: 38

Gly Gly Glu Pro Ser
1               5

<210> SEQ ID NO 39
<211> LENGTH: 7
<212> TYPE: PRT
<213> ORGANISM: Artificial sequence
<220> FEATURE:
<223> OTHER INFORMATION: Linker

<400> SEQUENCE: 39

Gly Gly Glu Gly Gly Gly Pro
1               5

<210> SEQ ID NO 40
<211> LENGTH: 12
<212> TYPE: PRT
<213> ORGANISM: Artificial sequence
<220> FEATURE:
<223> OTHER INFORMATION: Linker

<400> SEQUENCE: 40

Gly Gly Glu Gly Gly Gly Ser Glu Gly Gly Gly Ser
1               5                   10

<210> SEQ ID NO 41
<211> LENGTH: 8
<212> TYPE: PRT
<213> ORGANISM: Artificial sequence
<220> FEATURE:
<223> OTHER INFORMATION: Linker

<400> SEQUENCE: 41

Gly Gly Gly Ser Gly Gly Gly Gly
1               5

<210> SEQ ID NO 42
<211> LENGTH: 7
<212> TYPE: PRT
<213> ORGANISM: Artificial Sequence
```

-continued

```
<220> FEATURE:
<223> OTHER INFORMATION: Description of Artificial Sequence: Synthetic
      peptide

<400> SEQUENCE: 42

Gly Gly Glu Gly Gly Gly Pro
1               5

<210> SEQ ID NO 43
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 43

Gly Gly Glu Gly Gly Gly Ser Glu Gly Gly Gly Ser
1               5                   10

<210> SEQ ID NO 44
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 44

Gly Gly Gly Ser Gly Gly Gly Gly
1               5

<210> SEQ ID NO 45
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 45

Gly Leu Ser Pro Ile Val Trp Leu Ser Val
1               5                   10

<210> SEQ ID NO 46
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 46

Gly Leu Ser Pro Thr Val Trp Leu Leu Val
1               5                   10

<210> SEQ ID NO 47
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 47

Gly Gly Gly Ser
1
```

-continued

```
<210> SEQ ID NO 48
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 48

Thr Val Leu Arg Thr
1               5

<210> SEQ ID NO 49
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 49

Thr Val Ser Ser Ala Ser
1               5

<210> SEQ ID NO 50
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 50

Thr Val Leu Ser Ser Ala Ser
1               5

<210> SEQ ID NO 51
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 51

Gln Arg Leu Met Glu Asp Ile Cys Leu Pro Arg Trp Gly Cys Leu Trp
1               5                   10                  15

Glu Asp Asp Phe
            20
```